(12) United States Patent
Odland et al.

(10) Patent No.: US 9,138,559 B2
(45) Date of Patent: Sep. 22, 2015

(54) FLEXIBLE CATHETER

(75) Inventors: Rick M. Odland, Roseville, MN (US); Scott R. Wilson, Maple Grove, MN (US); Bradford G. Staehle, Minnetonka, MN (US)

(73) Assignee: Twin Star Medical, Inc, Minneapolis, MN (US)

( * ) Notice: Subject to any disclaimer, the term of this patent is extended or adjusted under 35 U.S.C. 154(b) by 421 days.

(21) Appl. No.: 12/997,999

(22) PCT Filed: Jun. 16, 2009

(86) PCT No.: PCT/US2009/047489
§ 371 (c)(1),
(2), (4) Date: Mar. 21, 2011

(87) PCT Pub. No.: WO2010/005714
PCT Pub. Date: Jan. 14, 2010

(65) Prior Publication Data
US 2011/0178505 A1 Jul. 21, 2011

Related U.S. Application Data

(60) Provisional application No. 61/061,895, filed on Jun. 16, 2008.

(51) Int. Cl.
*A61M 25/00* (2006.01)
*A61B 10/00* (2006.01)
*A61B 10/04* (2006.01)

(52) U.S. Cl.
CPC ........ *A61M 25/0043* (2013.01); *A61B 10/0045* (2013.01); *A61B 10/04* (2013.01); *A61M 2025/0042* (2013.01); *A61M 2025/0057* (2013.01)

(58) Field of Classification Search
CPC .................. A61B 10/0045; A61M 2025/0057; A61M 25/0043
USPC .......................... 604/523–524, 526–527, 285
See application file for complete search history.

(56) References Cited

U.S. PATENT DOCUMENTS

| | | | |
|---|---|---|---|
| 5,706,806 A | 1/1998 | Kissinger | |
| 5,916,147 A * | 6/1999 | Boury | 600/146 |
| 5,947,940 A * | 9/1999 | Beisel | 604/526 |
| 6,061,587 A | 5/2000 | Kucharczyk | |

(Continued)

FOREIGN PATENT DOCUMENTS

| | | |
|---|---|---|
| WO | 9200113 | 1/1992 |
| WO | 9907276 | 2/1999 |

(Continued)

*Primary Examiner* — Kevin C Sirmons
*Assistant Examiner* — Deanna K Hall
(74) *Attorney, Agent, or Firm* — Fredrikson & Byron, P.A.

(57) ABSTRACT

A catheter (100) is disclosed that includes a reinforced hollow fiber (114) and is suitable for insertion- in a body tissue in order to deliver and/or recover fluids to and/or from the tissue. In one embodiment, the catheter comprises a combination of catheter body (112), hollow fiber region (114), and reinforcing means (116), to provide a catheter having sufficient structural integrity for the hollow fiber region to be positioned within a body tissue, preferably without the need for ancillary devices such as introducers or protective sheaths, and to there be used for the purpose of delivering and/or recovering fluids from the surrounding tissue.

16 Claims, 38 Drawing Sheets

(56) References Cited

U.S. PATENT DOCUMENTS

| | | |
|---|---|---|
| 6,537,241 B1 | 3/2003 | Odland |
| 6,942,633 B2 | 9/2005 | Odland |
| 6,942,634 B2 | 9/2005 | Odland |
| 2003/0032942 A1* | 2/2003 | Theeuwes et al. ............ 604/537 |
| 2003/0181824 A1 | 9/2003 | Odland |
| 2004/0064129 A1 | 4/2004 | Deniega |

FOREIGN PATENT DOCUMENTS

| | | |
|---|---|---|
| WO | 03009882 | 6/2003 |
| WO | 03082074 | 10/2003 |

* cited by examiner

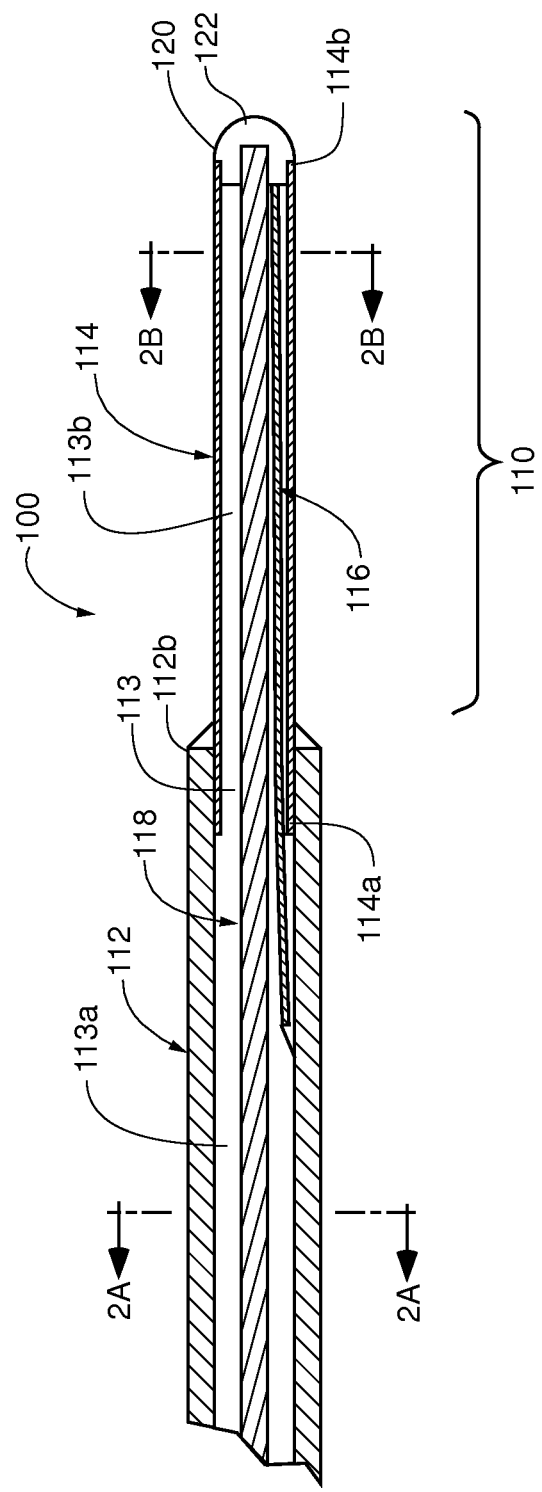

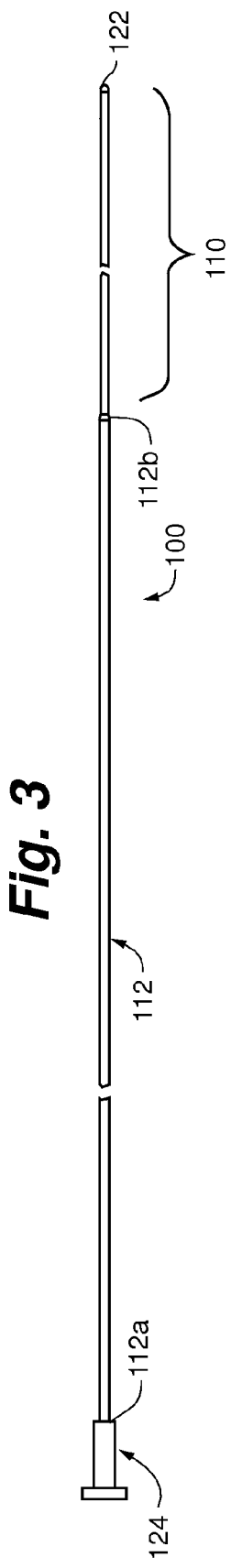

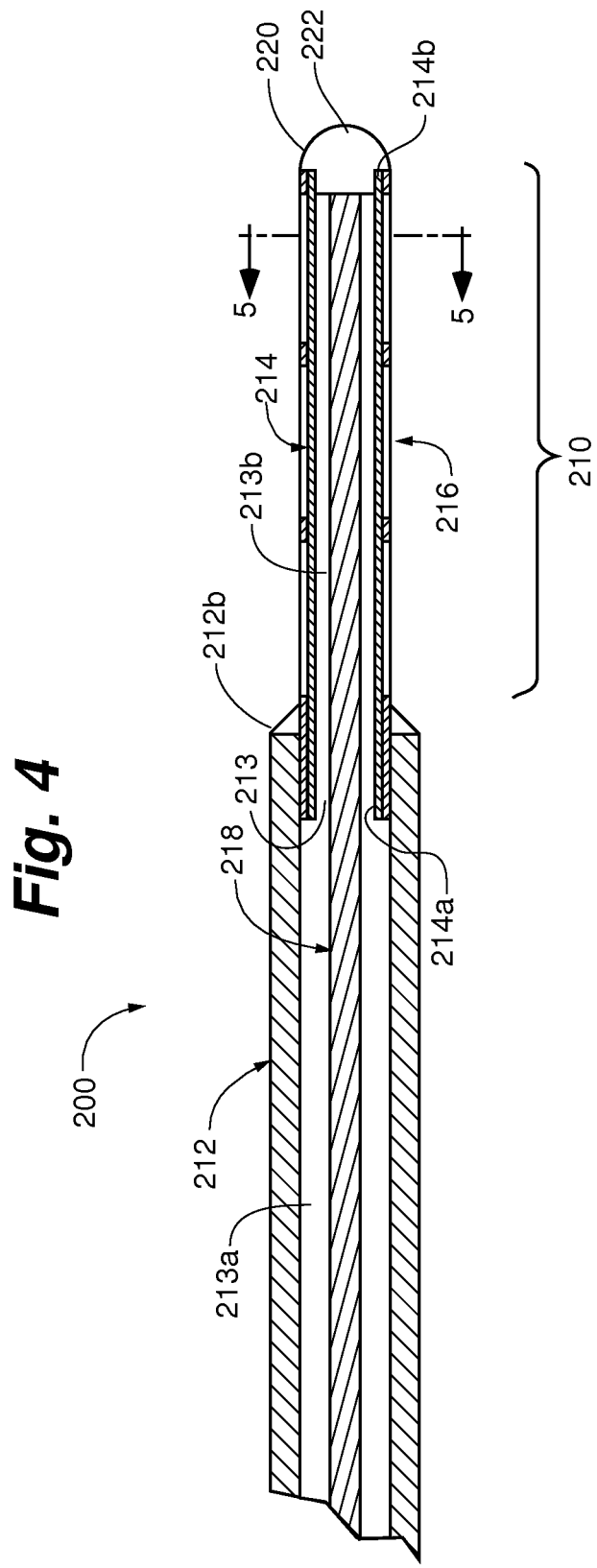

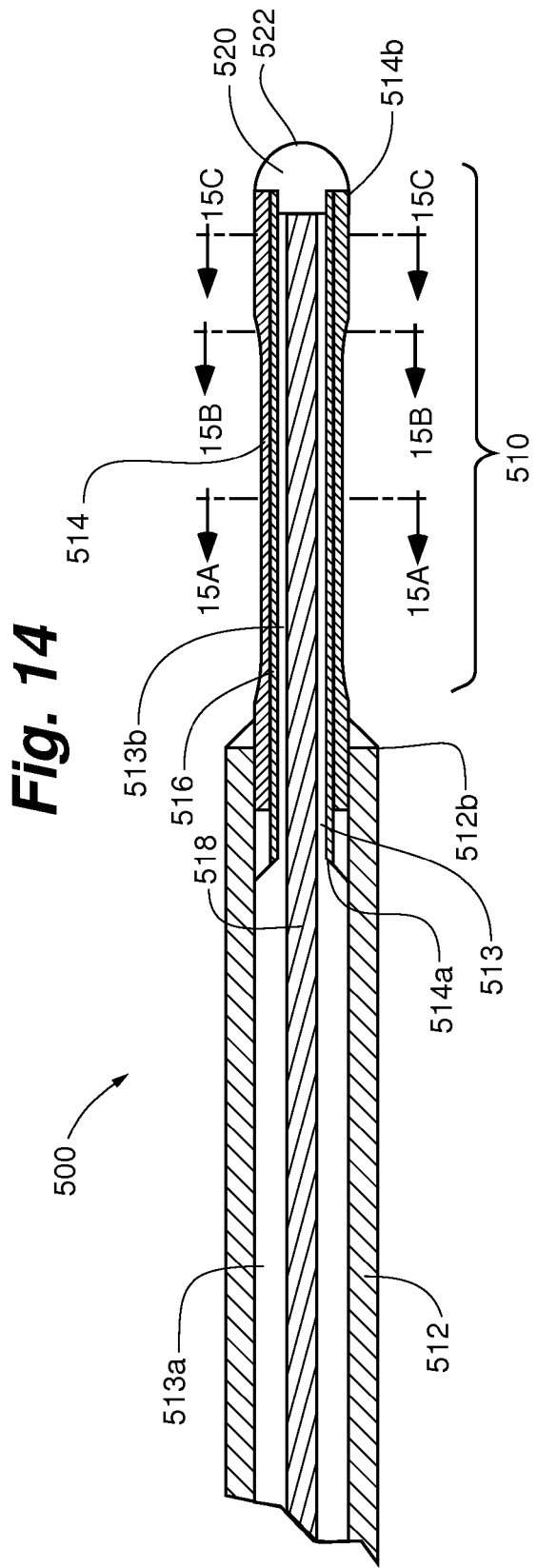

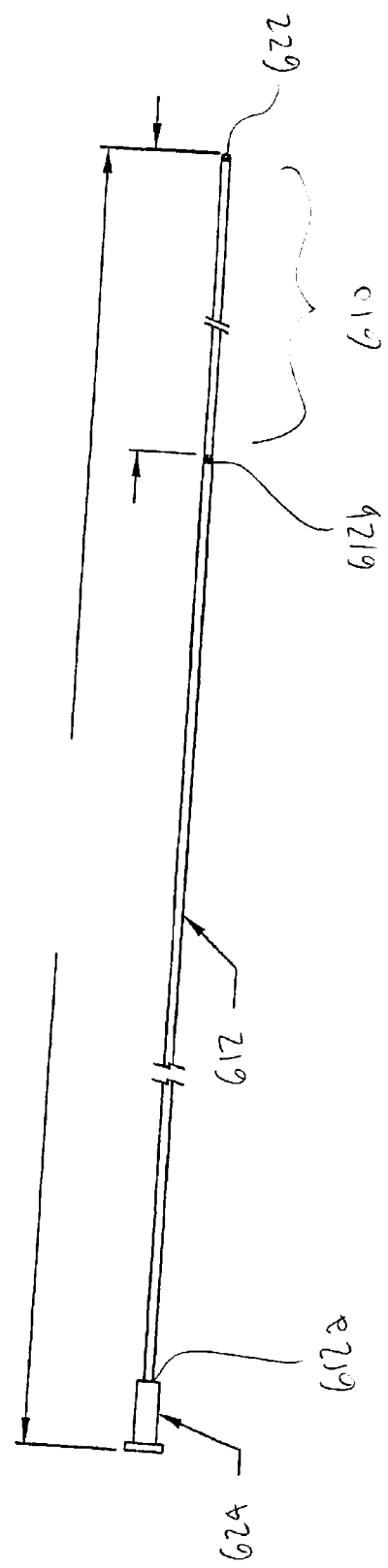

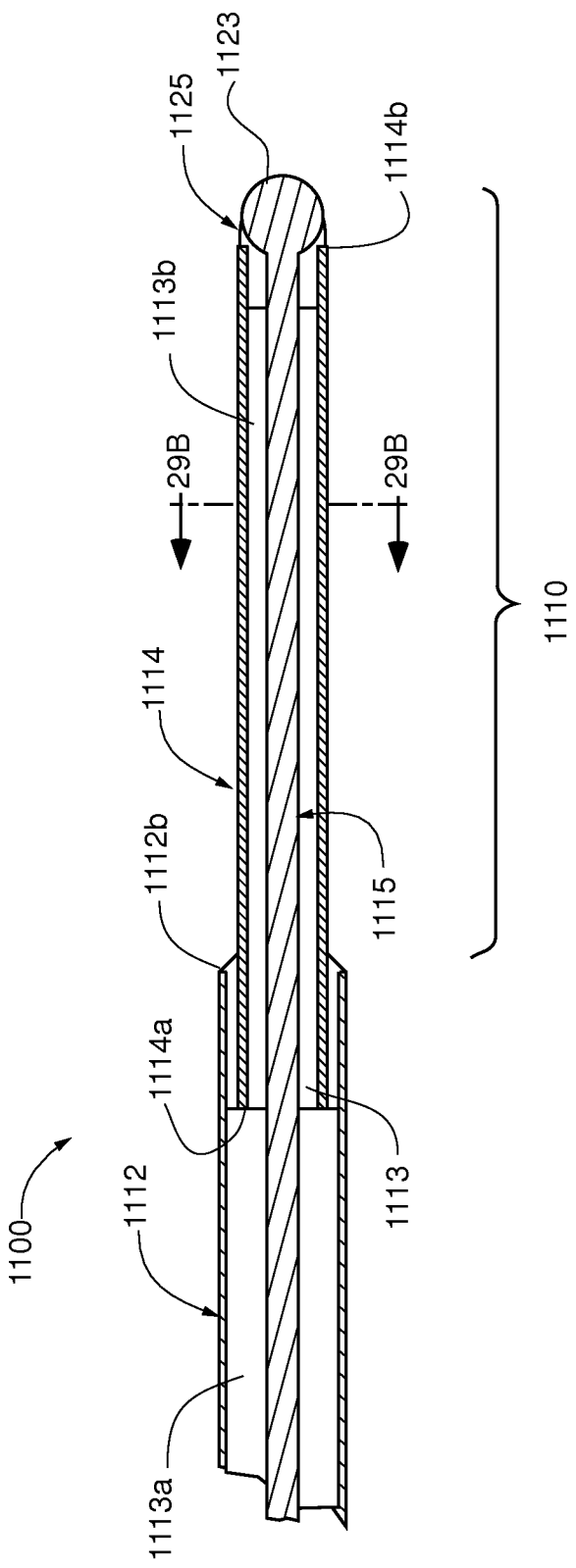

FLEXIBLE CATHETER

CROSS-REFERENCE TO RELATED APPLICATIONS

The present application claims priority to International Application No. PCT/US2009/047489 filed Jun. 16, 2009, which in turn claims priority to US Provisional Application No. 61/061,895 filed Jun. 16, 2008, the teachings of which are incorporated herein by reference.

FIELD OF THE INVENTION

The invention relates to catheters used for convection enhanced delivery of therapeutic fluids to specific remote anatomical locations in a mammalian body.

BACKGROUND

Millions of Americans are afflicted by neurogenerative and malignant diseases affecting the central nervous system (CNS). For many of these diseases, such as Parkinson's, Alzheimer's and high grade primary brain tumors, there is currently no curative therapy. An extensive effort has been taken to develop and test novel drugs, cell-based therapies, and gene therapy to treat these disorders. It is clear that even when effective therapeutic agents are identified, delivery into the CNS at therapeutic concentrations and sufficient distribution is a rate-limiting step to achieving clinical efficiency. The blood-brain barrier is composed of closely adhering endothelial cells, pericytes and astrocytes that tightly regulate the diffusion of molecules into the brain parenchyma. Substances with a molecular weight higher than 500 Daltons generally cannot cross the blood-brain barrier, while smaller molecules often can. Many drugs are unable to pass the barrier since the majority of them are heavier than 500 Daltons. Although efforts focused on achieving blood-brain barrier disruption and advances in endovascular delivery have shown promise, many agents such as tumor-targeted toxins, genetic vectors and chemotherapy have undesirable pharmacologic problems and systemic side effects when administered intravenously. Overcoming the drug-delivery obstacles to the CNS is a critical step in attaining better clinical outcomes.

Direct infusion of drugs into the brain parenchyma using convection-enhanced delivery (CED) results in the treatment of large areas of brain tissue and concentrates the infusate in situ, thereby circumventing the delivery obstacles posed by the blood-brain barrier and dilution of infusate in the blood. CED is a technique that relies on bulk flow to establish a pressure gradient over time, resulting in continuous convective flow and widespread distribution of the infusate to the affected areas of the brain. The extent of drug distribution using CED depends on many factors including: (1) interstitial pressure; (2) type of tissue infused (tumor, grey matter, white matter); (3) molecular weight of infusate; (4) volume and flow rate during administration; and (5) diameter/type of drug delivery catheter.

One limitation related to conventional CED treatment involves the backflow of infusate along the catheter body at increased infusion rates, which can be exasperated following introduction using a removable introducer. Backflow generally occurs as a result of excessive fluid infusion pressure at higher flow rates that preferentially drives the fluid up the catheter shaft as the path of least resistance. When using an introducer to place the catheter in tissue and due to the outer diameter of the introducer being necessarily greater than the outer diameter of the drug delivery catheter, this creates a post-introducer tissue compression, thereby creating a preferential gap and lower flow resistance along the catheter body, resulting in increased backflow or reflux of infusate during treatment at high injection flow rates as compared to catheters placed without introducers.

Another limitation relates to uneven distribution of infusate in brain tumor tissue as opposed to normal brain tissue. While the interstitial pressure of normal brain tissue is relatively low, (1-2 mm Hg), the interstitial pressure in brain tumor tissue can be over twenty-five times greater, which may account for uneven distribution and leakage of infusate into the subarachnoid space. This phenomenon is not surprising considering that most catheters used for CED have a single lumen from which infusate is delivered and the infusate may follow the path of lowest interstitial pressure. Additionally, it has been documented that multiport catheters may only infuse through one or two ports (that have least resistance to outflow) when eight are present, rendering the majority of ports useless for drug delivery. As an example, gliomas are composed of necrotic areas and regions of infiltrating tumor cells into the normal brain tissue, therefore the interstitial pressure varies greatly, creating counterproductive pressure gradients in peritumoral tissue. Use of CED in normal brain tissue with low flow rates (i.e., 0.1 µl/min) results in relatively homogenous distribution, but higher flow rates (i.e., 5 µl/min) results in reflux of the infusate back along the catheter track and away from the target tissue. Attempting to infuse large volumes, over a short time period, results in a deforming force on tissue, eventually narrowing the interstitial space and promoting a shear plane and tissue tearing. Therefore, a long administration time is required to administer even 1 ml of infusate because higher flow rates negate the desired distribution of drug using CED. What is clearly needed, therefore, and would be beneficial to treating brain tumor patients by CED, are new types of catheters and methods capable of increasing flow rate and decreasing total infusion time thereby shortening clinical procedures, while also minimizing reflux and allowing for more homogenous delivery of infusate.

Hollow fiber membranes are made from porous polymers and have been incorporated into catheters that improve the distribution of drugs administered directly into the central nervous system and other tissues. It has been found that using a porous polymer hollow fiber significantly increases the surface area of brain tissue that the drug or therapeutic fluid is infused into. Hollow fiber membranes create a very low pressure for fluid injection such that the risk for backflow is reduced while creating overall higher flow rates with the large surface area of the hollow fiber membrane. Dye was infused into a mouse brain by convection-enhanced delivery using a 28 gauge needle compared to a hollow fiber having a 3 mm length. Hollow fiber mediated infusion increased the volume of brain tissue labeled with dye by a factor of 2.7 times compared to using a needle. In order to determine if hollow fiber use could increase the distribution of gene therapy vectors, a recombinant adenovirus expressing the firefly luciferase reporter was injected into the mouse striatum. Gene expression was monitored using in vivo luminescent imaging. In vivo imaging revealed that hollow fiber mediated infusion of adenovirus resulted in gene expression that was an order of magnitude greater than when a conventional needle was used for delivery. To assess distribution of gene transfer, an adenovirus expression green fluorescent protein was injected into the striatum using a hollow fiber and a conventional needle. The hollow fiber greatly increased the area of brain transduced with adenovirus relative to a needle, transducing a significant portion of the injected hemisphere as determined by histological analysis.

On a separate subject, Applicant has previously disclosed and claimed various applications for the use of hollow fibers in various medical applications, including microdialysis, ultrafiltration and so forth. See, for instance, PCT application serial numbers PCT/US98/16416, filed 7 Aug. 1998, PCT/US03/08921, filed 21 Mar. 2003 and corresponding U.S. applications, all of which are incorporated herein by reference.

SUMMARY

The present invention provides a catheter that comprises a reinforced catheter including a hollow fiber suitable for insertion in a body tissue in order to deliver and/or recover (e.g., aspirate) fluids from the tissue, and which is then subsequently suitable for safe removal from the body tissue. In a preferred embodiment, the catheter comprises a combination of catheter body, hollow fiber region, and reinforcing component(s), which can be provided in any suitable combination and arrangement, to provide a catheter having sufficient structural integrity for the hollow fiber region to be positioned within a body tissue, optionally without the need for ancillary devices such as introducers or protective sheaths, and to there be used for the purpose of delivering and/or recovering fluids from the surrounding tissue, and then to be removed from the body tissue.

Typically, the catheter body will include a substantially solid body portion adapted to be coupled with and extend proximally from the hollow fiber region. Included also will be one or more reinforcing components, adapted to provide the hollow fiber region with sufficient properties (e.g., strength, flexibility and patency) to permit the hollow fiber region to remain in place and be used to deliver and/or recover fluids.

In one preferred embodiment, a removable rigid stylet can be included as well, and used to reinforce the catheter for insertion into tissue, e.g., by positioning the stylet within the catheter. It is generally desirable to remove the rigid stylet after positioning the catheter in the targeted tissue, so as to minimize tissue trauma from inadvertent movement of the catheter with a rigid stylet. In this manner, the catheter, including the hollow fiber region, can be retained in position after positioning of the catheter into body tissue using the rigid stylet, and prior to treatment (e.g., delivery and/or removal of fluid).

The hollow fiber region, in turn, will be of sufficient type, size, dimensions, configuration and porosity to permit it to remain positioned within a body tissue, including during stylet removal, and there used to deliver or recover fluids (including the recovery of fluid components, e.g., liquid and small solutes). The hollow fiber region can be coupled to the reinforcing component(s) and/or to the catheter body at or near its proximal end, and extend distally therefrom.

More preferably, one or more reinforcing components can be used to support the hollow fiber while in position and use within the body. Such reinforcing components can be provided in any particular form, e.g., in the form of one or more relatively flexible rods or tubes, which can be positioned in a suitable manner with respect to the catheter body and hollow fiber region, to permit the overall catheter, and particularly the distal hollow fiber region, to be used within and removed from tissue.

Reinforcing components can be provided by the use of materials having sufficient properties (e.g., rigidity, flexibility, strength, dimensions) to permit them to be positioned and used with respect to both the catheter body and hollow fiber region. Reinforcing components can be formed, for instance, of suitably flexible materials, including synthetic or nature materials such as metals, polymeric materials, and combinations thereof. A reinforcing component (e.g., flexible material) can be fabricated and used in any suitable shape, e.g., a solid rod or tubular, and can be positioned in any suitable manner with respect to both the catheter body and hollow fiber region, e.g., one or more rods or tubes can be positioned internally and/or externally to the catheter body and/or hollow fiber region.

The overall arrangement and use of reinforcing components with respect to the catheter body and hollow fiber region, will be sufficient to permit the catheter, including distal hollow fiber region, to withstand the tensile, compressive and other such pressures, as well as flexing and other motions necessary to insert the catheter into tissue, preferably without the need for ancillary devices or measures, and removal of the catheter form the body tissue.

In a particularly preferred embodiment, the reinforcing component(s) can be selected from the group consisting of:

1) a safety wire attached proximate the distal end of a hollow fiber membrane and inside the distal end of the catheter body, thereby serving to further secure the hollow fiber membrane to the catheter body;

2) a relatively flexible, slotted, external support that substantially surrounds the hollow fiber membrane and, and in turn, serves to protect and strengthen it;

3) a relatively flexible inner lumen tube that extends substantially the length of the catheter and that defines a central lumen, and which serves to protect and strengthen it;

4) an inner support tube configured to have at least a single opening to facilitate the delivery of infusate through the hollow fiber membrane, the tube being mounted within the hollow fiber membrane, extending substantially the length of the hollow fiber membrane and defining a lumen and serves to strengthen the catheter.

In other preferred embodiments, the invention provides one or more features selected from the group consisting of an introducer (e.g., introducing catheter), steerability, and the ability to prime the catheter in the course of its use.

Although generally designed to be sufficiently rigid for insertion in its own right, a preferred catheter of the current invention can be used together with one or more ancillary components, such as an introducing catheter or introducer.

Similarly, a catheter of the present invention is, or can be adapted to be sufficiently steerable to permit the user to direct the distal end in vivo. Various approaches for imparting directional control to the distal tip will become apparent to those skilled in the art, given the present description, and are incorporated herein by reference.

As also described herein, a preferred catheter of this invention is adapted to be primed prior to use, in order to minimize air in the catheter prior to injection, which can interfere with infusate distribution. Suitable priming means and processes are described herein and will also be apparent to those skilled in the art, given the present description.

BRIEF DESCRIPTION OF THE DRAWINGS

FIG. 1 is a longitudinal cross sectional view of the infusion section of an embodiment of a catheter of the present invention.

FIG. 3 is a plan view of the catheter of FIG. 1.

FIG. 4 is a longitudinal cross sectional view of the infusion section of an embodiment of a catheter of the present invention.

FIG. 14 is a longitudinal cross sectional view of the infusion section of an embodiment of a catheter of the present invention.

FIG. 20 is a plan view of the catheter of FIG. 18.

FIG. 29A is a longitudinal cross sectional view of the infusion section of an embodiment of a catheter of the present invention.

DETAILED DESCRIPTION

Figure 2A:
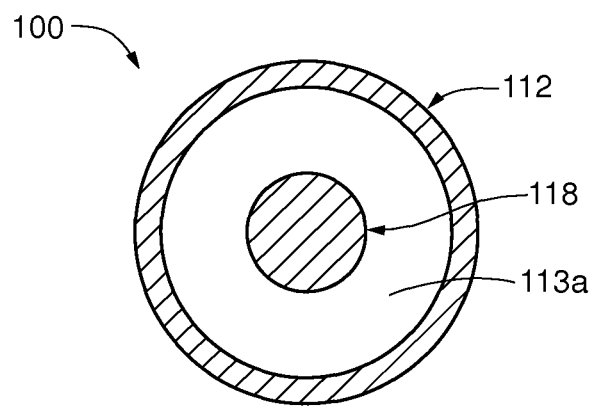
FIG. 2A is a lateral cross sectional view taken through lines 2A-2A of FIG. 1.

The particulars shown herein are by way of example and for purposes of illustrative discussion of the invention only and are presented in the cause of providing what is believed to be the most useful and readily understood description of the principles and conceptual aspects of the invention. In this regard, no attempt is made to show structural details of the invention in more detail than is necessary for the fundamental understanding of the invention, the description taken with the drawings making apparent to those skilled in the art how the several forms of the invention may be embodied in practice.
Selected Nomenclature
100 Catheter
110 Infusion Section
112 Catheter Body
112a Proximal End (Catheter Body)
112b Distal End (Catheter Body)
113 Lumen (Combined)
113a Lumen (Catheter Body)
113b Lumen (Hollow Fiber Membrane)
114 Hollow Fiber Membrane
114a Proximal End (Hollow Fiber Membrane)
114b Distal End (Hollow Fiber Membrane)
116 Safety Wire
118 Stylet
120 End Piece
122 Distal End
124 Connector
200 Catheter 210 Infusion Section
212 Catheter Body
212a Proximal End (Catheter Body)
212b Distal End (Catheter Body)
214 Hollow Fiber Membrane
214a Proximal End (Hollow Fiber Membrane)
214b Proximal End (Hollow Fiber Membrane)
216 External Support
218 Stylet
220 End Piece
222 Distal End
224 Connector
300 Catheter
310 Infusion Section
312 Catheter Body
312a Proximal End (Catheter Body)
312b Distal End (Catheter Body)
313 First Lumen
313a First Lumen (Catheter Body)
313b First Lumen (Hollow Fiber Membrane)
314 Hollow Fiber Membrane
314a Proximal End (Hollow Fiber Membrane)
314b Proximal End (Hollow Fiber Membrane)
315 Second Lumen
316 Inner Lumen Tube
318 Infusion Port
320 Distal End
324 Connector
326 Second Lumen Opening
400 Catheter
410 Infusion Section
412 Catheter Body
412a Proximal End (Catheter Body)
412b Distal End (Catheter Body)
413 Lumen
413a Lumen (Catheter Body)
413b Lumen (Hollow Fiber Membrane)
414 Hollow Fiber Membrane
414a Proximal End (Hollow Fiber Membrane)
414b Proximal End (Hollow Fiber Membrane)
416 Internal Support Tube
418 Stylet
420 End Piece
422 Distal End
424 Connector
500 Catheter
510 Infusion Section
512 Catheter Body
512a Proximal End (Catheter Body)
512b Distal End (Catheter Body)
513 Lumen
513a Lumen (Catheter Body)
513b Lumen (Hollow Fiber Membrane)
514 Hollow Fiber Membrane
514a Proximal End (Hollow Fiber Membrane)
514b Proximal End (Hollow Fiber Membrane)
516 Internal Support Tube
518 Stylet
520 End Piece
522 Distal End
524 Connector
600 Catheter
610 Infusion Section
612 Catheter Body
612a Proximal End (Catheter Body)
612b Distal End (Catheter Body)
613 Lumen
613a Lumen (Catheter Body)
613b Lumen (Hollow Fiber Membrane)
614 Hollow Fiber Membrane
614a Proximal End (Hollow Fiber Membrane)
614b Proximal End (Hollow Fiber Membrane)
616 Internal Support Tube
618 Stylet
620 End Piece
622 Distal End
624 Connector
700 Catheter
710 Infusion Section
712 Catheter Body
712a Proximal End (Catheter Body)
712b Distal End (Catheter Body)
713 First Lumen
714 Hollow Fiber Membrane
714a Proximal End (Hollow Fiber Membrane)
714b Proximal End (Hollow Fiber Membrane)
715 Second Lumen
716 Internal Support Tube
717 Open End (Delivery Tube)
718 Delivery Tube
719 Fluid Seal
720 End Piece
722 Distal End
724 Connector
800 catheter
810 infusion section
812 catheter body
812a proximal end
812b distal end
813 lumen
813a lumen
813b lumen
814 hollow fiber membrane
814a proximal end
814b distal end
819 fixed reinforcing stylet
820 end piece
824 fitting
831 fastener
900 catheter
910 infusion section
912 catheter body
912a proximal end
912b distal end
913 lumen
913a lumen
913b lumen
914 hollow fiber membrane
914a proximal end
914b distal end
916 internal support
917 removable priming tube
920 end piece
924 connector
1000 Infusion Pump
1100 catheter
1110 infusion section
1112 catheter body
1112a proximal end
1112b distal end
1113 lumen
1113a lumen
1113b lumen
1114 hollow fiber membrane 1114a proximal end
1114b distal end
1115 stylet
1115b distal end
1123 tip
1125 adhesive
1200 introducer
1202 needle
1202a proximal end
1202b distal end
1204 open tip
1206 hub
1208 vent plug
1210 locking portion
1212 sheath hub
1214 connector lock portion
1216 relief portion
1220 introducer assembly
1222 sheath
2000 syringe
2002 three-way valve
2004 two-way valve
2006 two-way valve
2008 three-way valve
2010 pressure transducer
2012 valve
2020 clamp
2022 pump
2024 flange
2026 clip
2027 holders
2028 lever
2030 plunger
2032 tubing holders
2034 bolus button
2040 nut
2042 catheter body
2044 ferrule
2046 receiving port
B Burr Hole
S Skull
Definitions "Catheter" is used in its general sense and refers to a conduit capable of transporting a substance or fluid to a remote location.

"Distal" means further from the point controlled by the operator (e.g., physician or technician) of a device.

"Fluid" means a substance offering no permanent resistance to change of shape, such as a gas or a liquid.

"Infusate" means medications and other substances which are beneficial to the healing process such as wound healing agents, pain medication and antibiotics.

"Proximal" means closer to the point controlled by the operator (e.g., physician or technician) of a device.

"Semi-Permeable Membrane" means a porous or semi-permeable barrier permitting controlled passage of fluid molecules under certain conditions.

"Therapeutic Fluid" means medications and other substances which are beneficial to the healing process such as wound healing agents, pain medication and antibiotics.

"Topical" means relating to a particular area at the surface and immediately underneath, such as an area exposed as the result of a wound.

"μm" means micron.

Construction

FIG. 1 is a longitudinal cross sectional view of the infusion section 110 of an embodiment of a catheter 100 of the present invention. An elongated catheter body 112 is made of any suitable flexible tubing material such as a medical grade urethane or other polymers and defines a proximal end 112a, a distal end 112b and a lumen 113a capable of fluid communication, extending the length of the catheter body 112. The infusion section 110 is defined by a hollow fiber membrane 114 which is attached to the distal end 112b of the catheter body 112 using a suitable medical grade adhesive such as epoxies or urethanes and defines a proximal end 114a, a distal end 114b and a lumen 113b. The lumen 113b of the hollow fiber membrane 114 is continuous with the lumen 113a of the catheter body 112 to form lumen 113 and allows fluid communication between the proximal end 112a of the catheter body 112 and the distal end 114b of the hollow fiber membrane 114. A reinforcing component in the form of safety wire 116 is attached proximate the distal end 114b of the hollow fiber membrane 114 and inside the distal end 112b of the catheter body 112 and serves to further secure the hollow fiber membrane 114 to the catheter body 112. An end piece 120 is attached to the distal end 114b of the hollow fiber membrane 114 and prevents the direct escape or intrusion of fluid from the lumen 113b. The catheter 100 is designed to accommodate a removable stylet 118 through the lumen 113 which serves to stiffen the hollow fiber membrane 114 and catheter body 112, thus facilitating introduction into a patient during treatment. The safety wire 116 also facilitates catheter 100 introduction into a patient and the removal of the stiffening stylet 118 prior to infusion and facilitating the save removal of the catheter 100 from the patient following completion of treatment. The end piece 120 therefore also provides a stop for the stylet 118 allowing it to sufficiently stiffen the infusion section 110 to be self-introducing into brain or other tissues. A self introducing catheter 100 is advantageous for several reasons: (1) the procedure can be completed in less time; (2) the likelihood of infection is reduced due to fewer required instruments; and (3) reduced backflow of therapeutic fluid during treatment due to less tissue compression between the catheter 100 and tissue resulting from direct introduction.

Figure 2B:
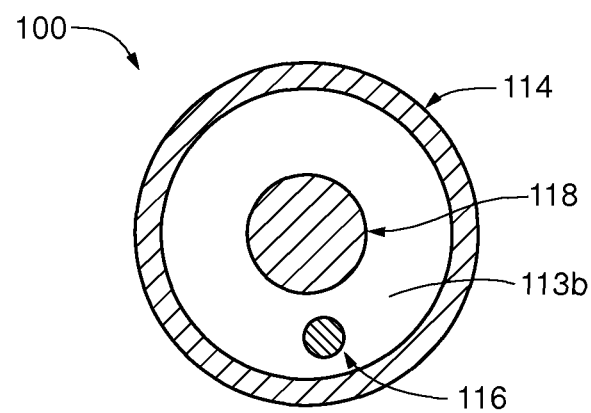
FIG. 2B is a lateral cross sectional view of the infusion section of the catheter of FIG. 1 taken through lines 2B-2B of FIG. 1.

FIG. 2A is a lateral cross sectional view taken through lines 2A-2A of FIG. 1 and illustrates the catheter body 112 defining the lumen 113a. The stylet 118 is seen extending through the lumen 113a. Similarly, FIG. 2B shows a lateral cross sectional view of the infusion section taken through lines 2B-2B of FIG. 1, with the safety wire 116 and stylet 118 extending through the lumen 113b. FIG. 3 is a view of the entire catheter 100, showing, inter alia, the connector 124 attached to the proximal end 112a of the catheter body 112.

FIG. 4 shows the infusion section 210 of another embodiment of a catheter 200 of the present invention. An elongated catheter body 212 is made of any suitable flexible tubing material such as a medical grade urethane or other polymers and defines a proximal end 212a and a distal end 212b and a lumen 213a capable of fluid communication, extending the length of the catheter body 212. The infusion section 210 is defined by a hollow fiber membrane 214 which is attached to the distal end 212b of the catheter body 212 using a suitable medical grade adhesive such as epoxies and urethanes and defines a proximal end 214a, a distal end 214b and a lumen 213b. The lumen 213b of the hollow fiber membrane 214 is continuous with the lumen 213a of the catheter body 212 to form lumen 213 and allows fluid communication between the proximal end 212a of the catheter body 212 and the distal end 214b of the hollow fiber membrane 214. A reinforcing component is provided in the form of relatively flexible, slotted, external support 216 made of polymers or metal surrounds the hollow fiber membrane 214 and serves to protect and strengthen the catheter 200, thus facilitating catheter 200 introduction into a patient and facilitating the removal of the stiffening stylet 218 prior to infusion and facilitating the save removal of the catheter 200 from the patient following completion of treatment. The external support 216 may include other types of openings other than slots, such as circles or triangles as may be needed to create the appropriate, flexibility, strength and openness. Alternatively, the external support 216 can be fabricated from polymer or metallic wires to create a braided tube (not shown) having sufficient strength, openness and flexibility. An end piece 220 is attached to the distal end 214*b* of the hollow fiber membrane 214 and external support 216 and prevents the escape or intrusion of fluid from the lumen 213*b*. The catheter 200 is designed to accommodate a removable stylet 218 through the lumen 213 which serves to significantly stiffen the catheter 200, thus facilitating introduction into a patient during treatment. The end piece 220 therefore also provides a stop for the stylet 218 allowing it to sufficiently stiffen the catheter 200 to be self-introducing into brain or other tissues, thus relegating the need for a separate introducer. A self introducing catheter 200 is advantageous for several reasons: (1) the procedure can be completed in less time; (2) the likelihood of infection is reduced due to fewer required instruments; and (3) reduced backflow of therapeutic fluid during treatment due to less tissue compression between the catheter 200 and tissue resulting from direct introduction.

Figure 5:
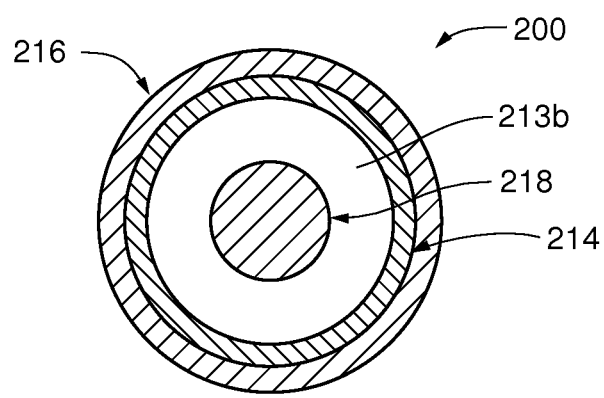
FIG. 5 is a lateral cross sectional view of the infusion section of the catheter of FIG. 4 taken through lines 5-5 of FIG. 4.
Figure 6:
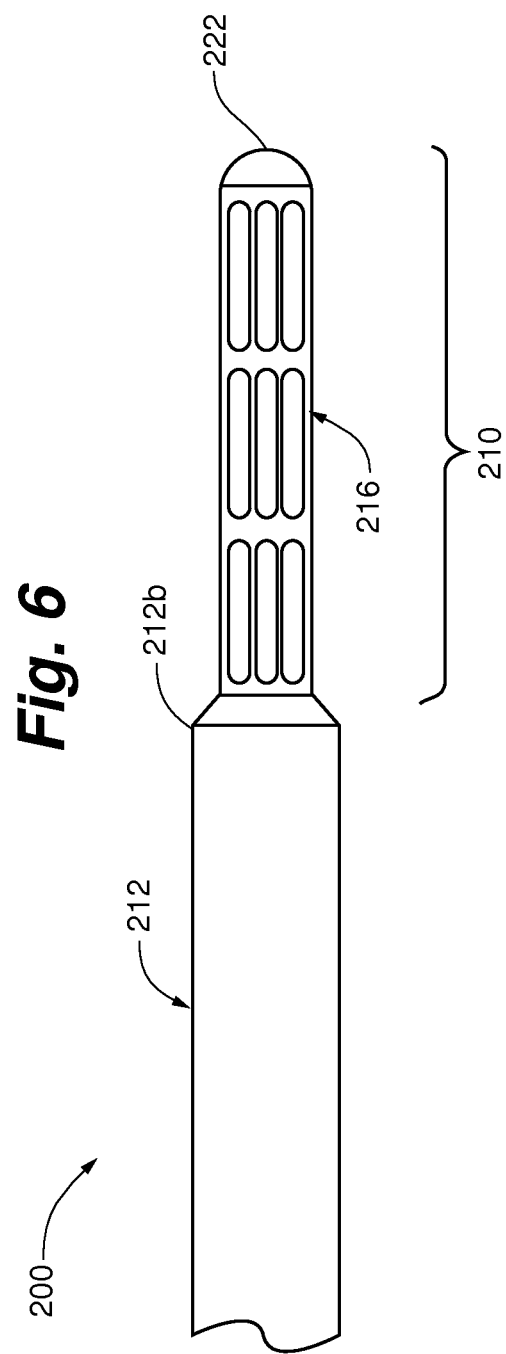
FIG. 6 is an external view of the infusion section of an embodiment of a catheter of the present invention.
Figure 7:
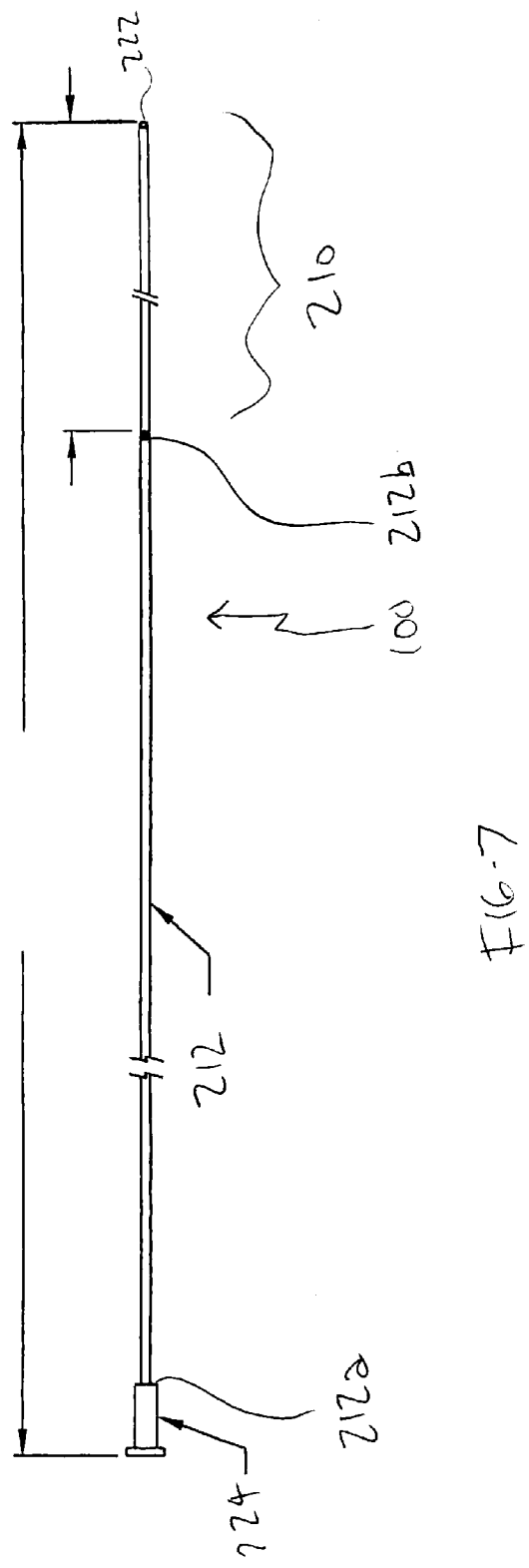
FIG. 7 is a plan view of the catheter of FIG. 4.

FIG. 5 is a lateral cross sectional view taken through infusion section 210 and illustrates the external support 216 surrounding the hollow fiber membrane 214 defining the lumen 213*b*. The stylet 218 is seen extending through the lumen 213*a*. FIG. 6 shows an external view of the infusion section 210 including the external support 216. FIG. 7 is a view of the entire catheter 200, showing, inter alia, the connector 224 attached to the proximal end 212*a* of the catheter body 212.

Figure 8:
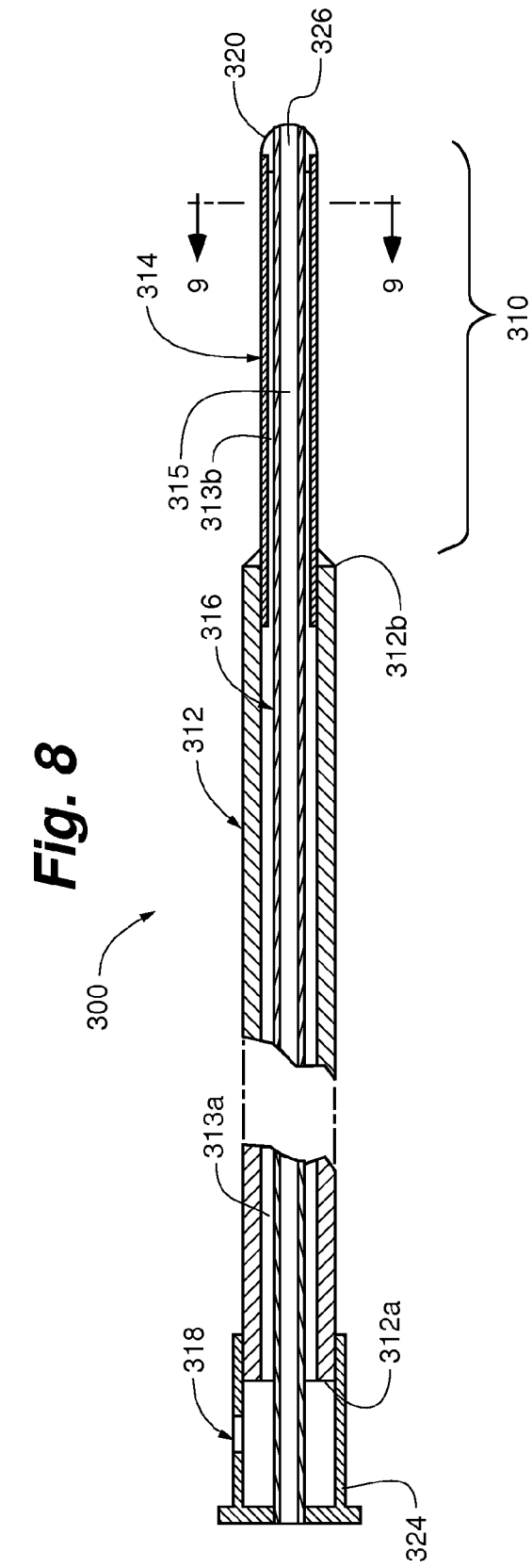
FIG. 8 is a longitudinal cross sectional view of the infusion section of an embodiment of a catheter of the present invention.

FIG. 8 shows yet another embodiment of a catheter 300 of the present invention. An elongated catheter body 312 is made of any suitable flexible tubing material such as a medical grade urethane or other polymers and defines a proximal end 312*a*, a distal end 312*b* and a lumen 313*a* capable of fluid communication, extending the length of the catheter body 312. The infusion section 310 is defined by a hollow fiber membrane 314 which is attached to the distal end 312*b* of the catheter body 312 using a suitable medical grade adhesive such as epoxies or urethanes and defines a proximal end 314*a*, a distal end 314*b* and a lumen 313*b*. The lumen 313*b* of the hollow fiber membrane 314 is continuous with the lumen 313*a* of the catheter body 312 and allows fluid communication between the proximal end 312*a* of the catheter body 312 and the distal end 314*b* of the hollow fiber membrane 314. A reinforcing component is provided in the form of relatively flexible inner lumen tube 316 which extends the length of the catheter 300 and defines a central lumen 315 and serves to provide a lumen to the distal end 326 of the catheter 300 and provide strength to the hollow fiber membrane 314 upon removal of instruments from the inner lumen tube 316 or removal of catheter from body tissue after treatment. The inner lumen tube 316 terminates at the distal end 320 at a distal lumen opening 326 thus allowing the catheter 300 to be additionally used for a removable stylet with a needle point (not shown) at the tip, projecting beyond opening 326, for introduction of a catheter 300 into tissues requiring some cutting for ease of placement. After removing the needle point stylet (not shown), a removable anchoring wire (not shown) can be introduced through the inner lumen tube 316 to keep the catheter 300 from being displaced during drug infusion. The removable anchoring wire (not shown) could take various forms such that it can be passed down the inner lumen tube 316 and then deploys to an anchoring shape such as a hook (not shown) or spiral (not shown) shape. When removing the catheter 300 from tissue, the anchoring wire (not shown) would be pulled out of the tissue and then followed by the catheter 300 removal. Alternatively, for those applications not requiring anchoring, the inner tube lumen 316 could be used for the introduction of other medical instruments for tissue monitoring such as pressure or the aspiration of fluids. A self introducing catheter 300 is advantageous for several reasons: (1) the procedure can be completed in less time; (2) the likelihood of infection is reduced due to fewer required instruments; and (3) reduced reflux of therapeutic fluid during treatment due to less tissue compression between the catheter 300 and tissue resulting from direct introduction.

Figure 9:
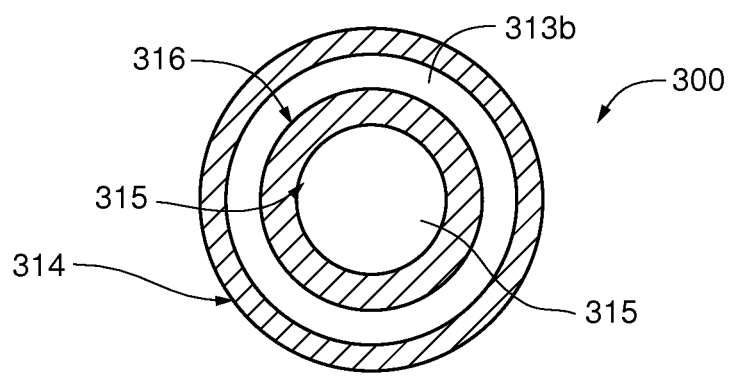
FIG. 9 is a lateral cross sectional view of the infusion section of the catheter of FIG. 8 taken through lines 9-9 of FIG. 8.
Figure 10:
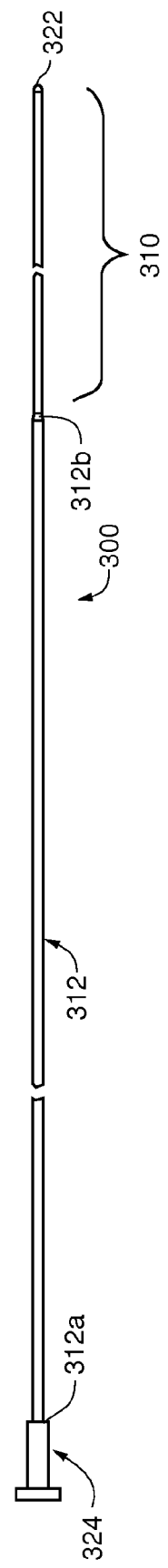
FIG. 10 is a plan view of the catheter of FIG. 8.

FIG. 9 is a lateral cross sectional view taken through infusion section 310 and illustrates the hollow fiber membrane 314, the lumen 313*b*, the internal support 316 and central lumen 315. FIG. 10 is a view of the entire catheter 300 showing, inter alia, the connector 324 attached to the proximal end 312*a* of the catheter body 312.

Figure 11:
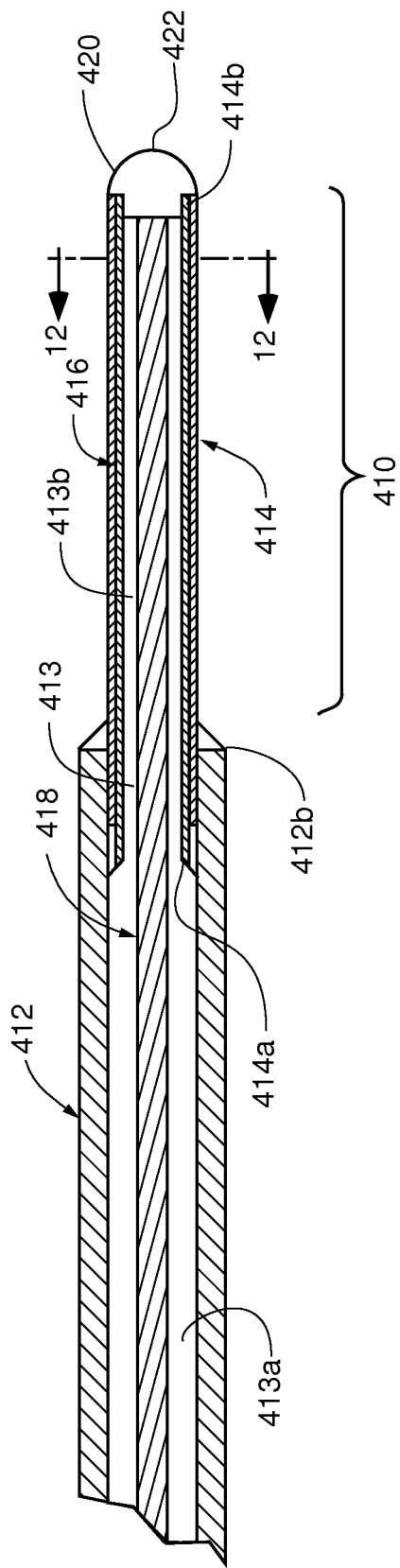
FIG. 11 is a longitudinal cross sectional view of the infusion section of an embodiment of a catheter of the present invention.

FIG. 11 shows a further alternative embodiment of a catheter 400 of the present invention. An elongated catheter body 412 is made of any suitable flexible tubing material such as a medical grade urethane or other polymer and defines a proximal end 412*a*, a distal end 412*b* and a lumen 413*a* capable of fluid communication, extending the length of the catheter body 412. The infusion section 410 is defined by a hollow fiber membrane 414 which is attached to the distal end 412*b* of the catheter body 412 using a suitable medical grade adhesive such as epoxies and urethanes and defines a proximal end 414*a*, a distal end 414*b* and a lumen 413*b*. The lumen 413*b* of the hollow fiber membrane 414 is continuous with the lumen 413*a* of the catheter body 412 to form lumen 413 and allows fluid communication between the proximal end 412*a* of the catheter body 412 and the distal end 414*b* of the hollow fiber membrane 414. A reinforcing component is provided in the form of an inner support tube 416 configured to have at least a single opening (not shown) to facilitate the delivery of infusate through the hollow fiber membrane 414 and is mounted within the hollow fiber membrane 414, extends the length of the hollow fiber membrane 414 and defines a lumen 413*b* and serves to strengthen the catheter 400, thus facilitating catheter 400 introduction into a patient and facilitating the removal of the stiffening stylet 418 prior to infusion and facilitating the save removal of the catheter 400 from the patient following completion of treatment. The internal support 416 may include other types of openings other than a single hole, such as circles, slots or triangles as may be needed to create the appropriate, flexibility, strength and openness. Alternatively, the internal support 416 can be fabricated from polymer or metallic wires to create a braided tube (not shown) having sufficient strength, openness and flexibility. The catheter 400 is designed to accommodate a removable stylet 418 through the lumen 413 which serves to significantly stiffen the infusion section 410, thus facilitating introduction into a patient during treatment. An end piece 420 is attached to the distal end 414*b* of the hollow fiber membrane 414 and prevents the direct escape or intrusion of fluid from the lumen 413. A self introducing catheter 400 is advantageous for several reasons: (1) the procedure can be completed in less time; (2) the likelihood of infection is reduced due to fewer required instruments; and (3) reduced reflux of therapeutic fluid during treatment due to less tissue compression between the catheter 400 and tissue resulting from direct introduction.

Figure 12:
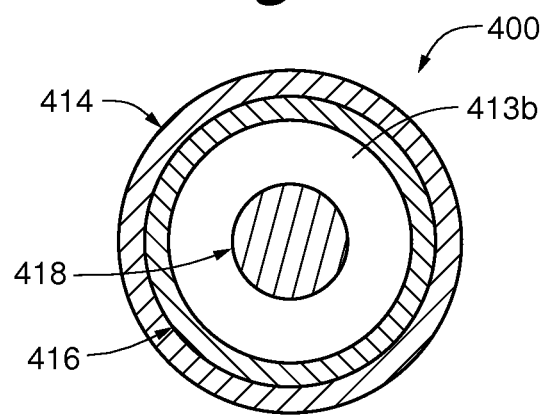
FIG. 12 is a lateral cross sectional view of the infusion section of the catheter of FIG. 11 taken through lines 12-12 of FIG. 11.
Figure 13:
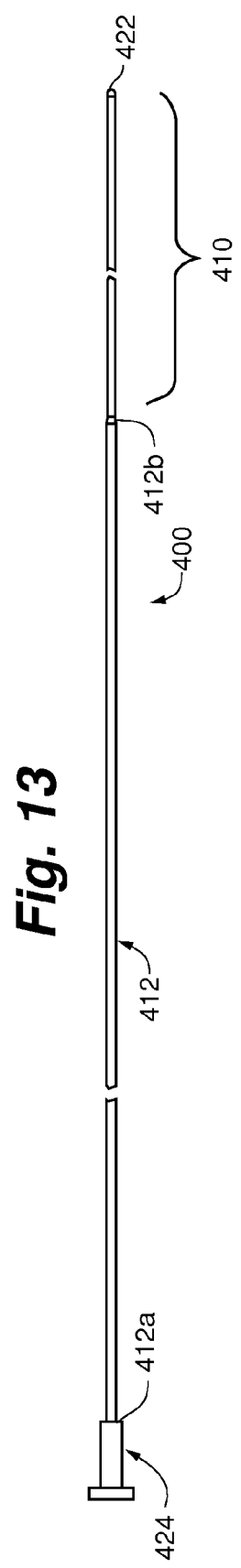
FIG. 13 is a plan view of the catheter of FIG. 11.

FIG. 12 is a lateral cross sectional view taken through infusion section 410 and illustrates the hollow fiber membrane 414, the lumen 413*b*, the internal support 416 and removable stylet 418. FIG. 13 is a view of the entire catheter 400 showing, inter alia, the connector 424 attached to the proximal end 412a of the catheter body 412.

FIG. 14 shows an additional embodiment of a catheter 500 of the present invention. An elongated catheter body 512 is made of any suitable flexible tubing material such as a medical grade urethane or other polymers and defines a proximal end 512a, a distal end 512b and a lumen 513a capable of fluid communication, extending the length of the catheter body 512. The infusion section 510 is defined by a hollow fiber membrane 514 which is attached to the distal end 512b of the catheter body 512 using a suitable medical grade adhesive such as epoxies and urethanes and defines a proximal end 514a, a distal end 514b and a lumen 513b. The lumen 513b of the hollow fiber membrane 514 is continuous with the lumen 513a of the catheter body 512 to form lumen 513 and allows fluid communication between the proximal end 512a of the catheter body 512 and the distal end 514b of the hollow fiber membrane 514. A reinforcing component is provided in the form of inner support tube 516 and is configured to have at least a single opening (not shown) to facilitate the delivery of infusate through the hollow fiber membrane and is mounted within the hollow fiber membrane 514, extends the length of the hollow fiber membrane 514 and defines a lumen 513b and serves to strengthen the catheter 500, thus facilitating catheter 500 introduction into a patient during treatment and upon removing the stiffening stylet 518 prior to infusion or upon removing the catheter 500 from the patient following completion of treatment. The internal support 516 may include other types of openings other than a single hole, such as circles, slots or triangles as may be needed to create the appropriate, flexibility, strength and openness. Alternatively, the internal support 516 can be fabricated from polymer or metallic wires to create a braided tube (not shown) having sufficient strength, openness and flexibility. The catheter 500 is designed to accommodate a removable stylet 518 through the lumen 513 which serves to significantly stiffen the infusion section 510 and catheter body 512, thus facilitating introduction into a patient during treatment. An end piece 520 is attached to the distal end 514b of the hollow fiber membrane 514 and prevents the escape or intrusion of fluid from the lumen 513. A self introducing catheter 500 is advantageous for several reasons: (1) the procedure can be completed in less time; (2) the likelihood of infection is reduced due to fewer required instruments; and (3) reduced reflux of therapeutic fluid during treatment due to less tissue compression between the catheter 500 and tissue resulting from direct introduction.

Figure 15A:
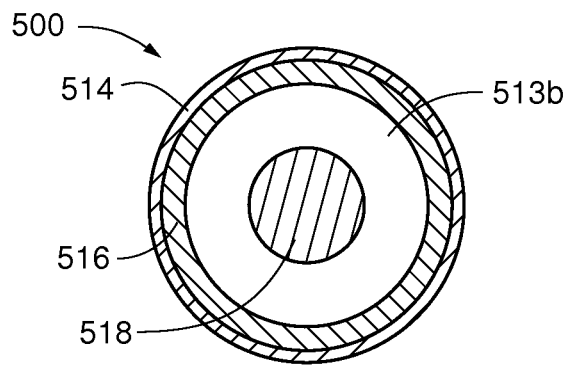
FIG. 15A is a lateral cross sectional view of the infusion section of the catheter of FIG. 14 taken through the lines 15A-15A.
Figure 15B:
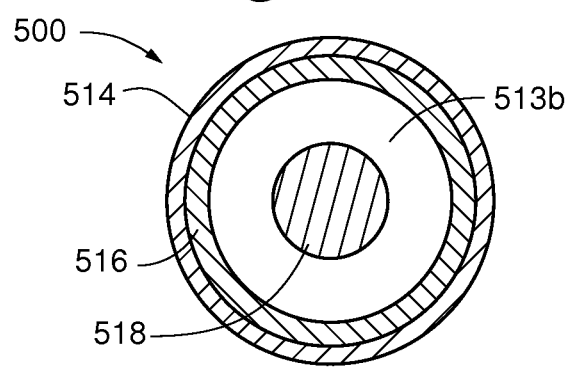
FIG. 15B is a lateral cross sectional view of the infusion section of the catheter of FIG. 14 taken through the lines 15B-15B.
Figure 15C:
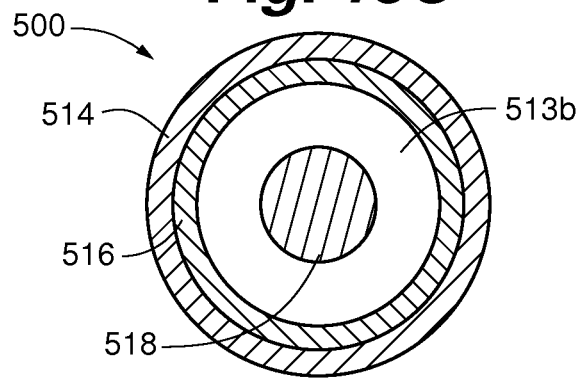
FIG. 15C is a lateral cross sectional view of the infusion section of the catheter of FIG. 14 taken through the lines 15C-15C.
Figure 16:
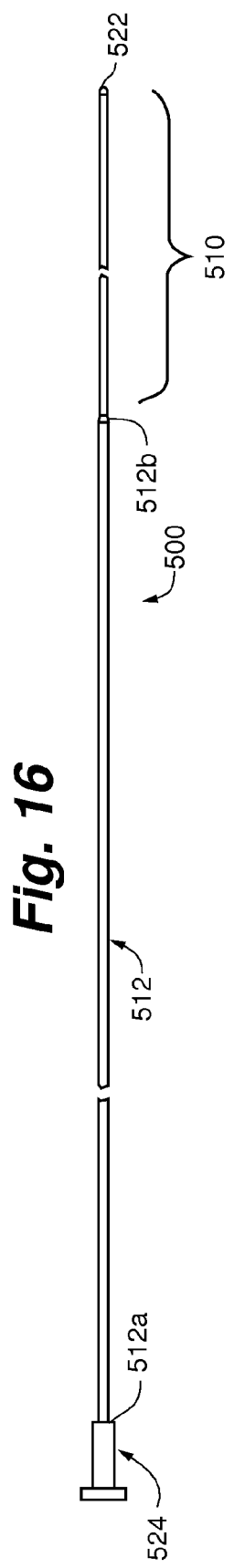
FIG. 16 is a plan view of the catheter of FIG. 14.

FIG. 15A is a lateral cross sectional view taken infusion section 510 and illustrates the hollow fiber membrane 514, the lumen 513b, the internal support 516 and removable stylet 518. FIG. 15B is a lateral cross sectional view taken infusion section 510 and illustrates the hollow fiber membrane 514, the lumen 513b, the internal support 516 and removable stylet 518. FIG. 15C is a lateral cross sectional view taken infusion section 510 and illustrates the hollow fiber membrane 514, the lumen 513b, the internal support 516 and removable stylet 518. It is noted that the hollow fiber membrane 514 becomes progressively thicker in a distal direction as illustrated in FIGS. 15A-15C. Not shown specifically, it is noted that the hollow fiber membrane 514 becomes symmetrically progressively thicker in a proximal direction as seen in FIG. 14. FIG. 16 is a view of the entire catheter 500 showing, inter alia, the connector 524 attached to the proximal end 512a of the catheter body 512. It should also be mentioned that while not shown, the invention contemplates and therefore is within the scope of a non-symmetrically and non-uniformly tapered hollow fiber membrane 514. FIG. 16 is a view of the entire catheter 400 showing, inter alia, the connector 524 attached to the proximal end 512a of the catheter body 512.

Figure 17:
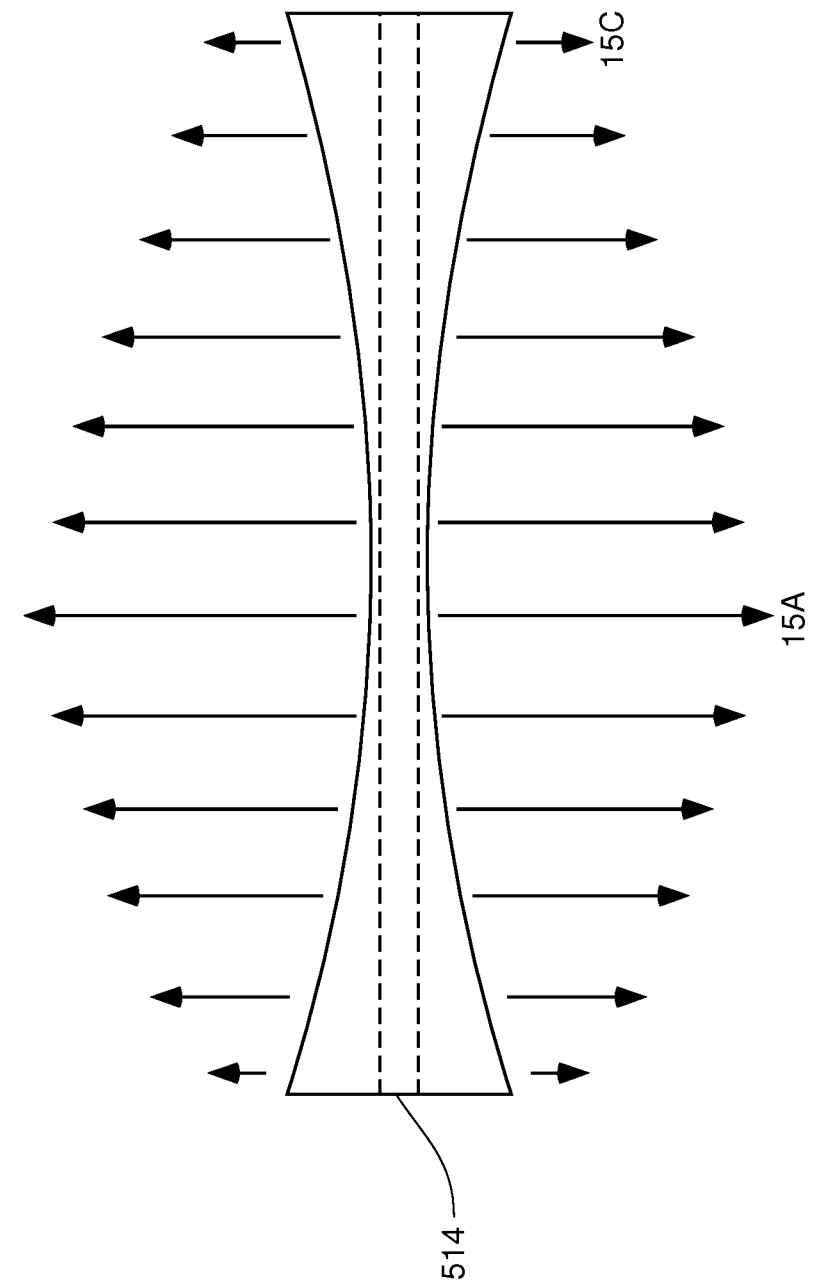
FIG. 17 illustrates the infusate distribution pattern or plume of the catheter shown in FIGS. 14-16.

FIG. 17 illustrates the infusate distribution pattern or plume of the infusion section 510 of catheter 500 shown in FIGS. 14-16. It is noted that the thinnest section of the hollow fiber membrane 514 as illustrated in FIG. 15A, represents the furthest point of infusate distribution from the hollow fiber membrane 514 while the closest point of infusate distribution corresponds with the thickest section of hollow fiber membrane 514, as illustrated in FIG. 15C. The intermediate section of hollow fiber membrane 514 represents an intermediate point of infusate distribution, as illustrated in FIG. 15B. The reason for this distribution pattern is that the thinner sections of the hollow fiber membrane 514 offer less resistance to the outflow of infusate and thus increases the flow at these reduced resistance regions along the length of the hollow fiber membrane 514. One of the advantages conferred by using hollow fiber membrane technology is that while the infusate will distribute further through a thinner section, the infusate is released along the length of the hollow fiber membrane at similar pressures creating a reliable distribution pattern. In some instances, anatomy targeted for treatment may be more effective with an infusate distribution pattern which more closely fits the shape of the tissue targeted for treatment. One example is tumors which tend to be more spherical in shape and thus the ideal drug distribution pattern would be greater at the center of the hollow fiber membrane 514 and decreases towards each end.

Figure 18:
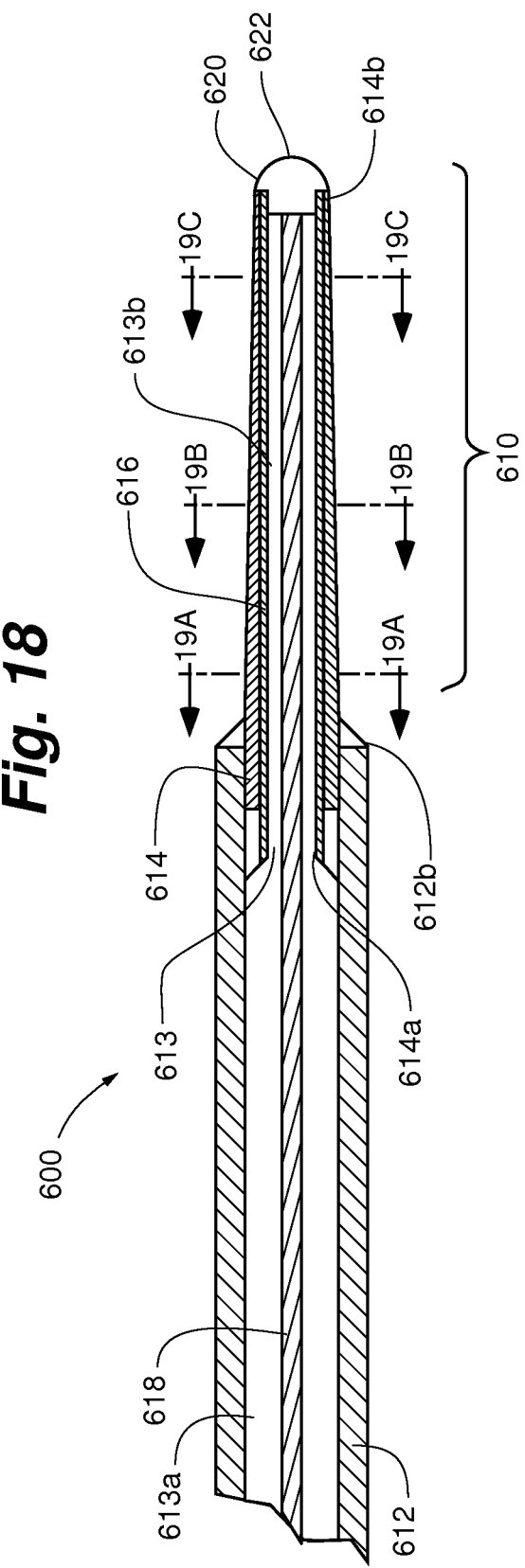
FIG. 18 is a longitudinal cross sectional view of the infusion section of an embodiment of a catheter of the present invention.

FIG. 18 shows another embodiment of a catheter 600 of the present invention. An elongated catheter body 612 is made of any suitable flexible tubing material such as a medical grade urethane or other polymers and defines a proximal end 612a, a distal end 612b and a lumen 613a capable of fluid communication, extending the length of the catheter body 612. The infusion section 610 is defined by a hollow fiber membrane 614 which is attached to the distal end 612b of the catheter body 612 using a suitable medical grade adhesive such as epoxies or urethanes and defines a proximal end 614a, a distal end 614b and a lumen 613b. The lumen 613b of the hollow fiber membrane 614 is continuous with the lumen 613a of the catheter body 612 to form lumen 613 and allows fluid communication between the proximal end 612a of the catheter body 612 and the distal end 614b of the hollow fiber membrane 614. A reinforcing component is provided as an inner support tube 616 configured to have at least a single opening (not shown) to facilitate the delivery of infusate through the hollow fiber membrane 614 and is mounted within the hollow fiber membrane 614, extends at least the length of the hollow fiber membrane 614 and defines a lumen 613b and serves to strengthen the hollow fiber membrane 614, thus facilitating introduction into a patient during treatment and upon removing the stiffening stylet 618 prior to infusion or upon removing catheter 600 from the patient following completion of treatment. The internal support 616 may include other types of openings other than a single hole, such as circles, slots or triangles as may be needed to create the appropriate flexibility, strength and openness. Alternatively, the internal support 616 can be fabricated from polymer or metallic wires to create a braided tube (not shown) having sufficient strength, openness and flexibility. The catheter 600 is designed to accommodate a removable stylet 618 through the lumen 613 which serves to significantly stiffen the infusion section 610, thus facilitating catheter 600 introduction into a patient during treatment. An end piece 620 is attached to the distal end 614b of the hollow fiber membrane 614 and prevents the escape or intrusion of fluid from the lumen 613. A self introducing catheter 600 is advantageous for several reasons: (1) the procedure can be completed in less time; (2) the likelihood of infection is reduced due to fewer required instruments; and (3) reduced reflux of therapeutic fluid during treatment due to less tissue compression between the catheter 600 and tissue resulting from direct introduction.

Figure 19A:
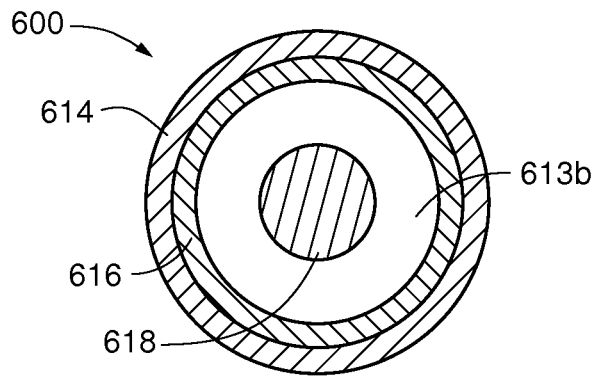
FIG. 19A is a lateral cross sectional view of the infusion section of the catheter of FIG. 18 taken through the lines 19A-19A.
Figure 19B:
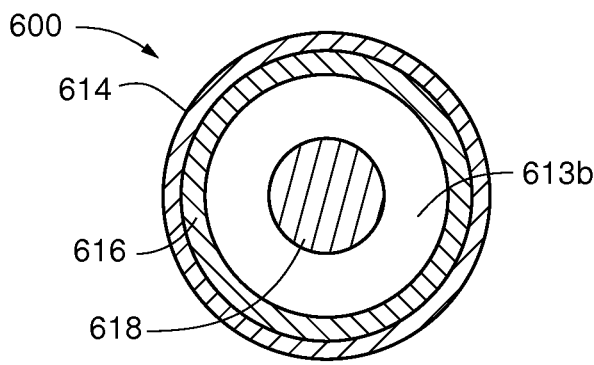
FIG. 19B is a lateral cross sectional view of the infusion section of the catheter of FIG. 18 taken through the lines 19B-19B.
Figure 19C:
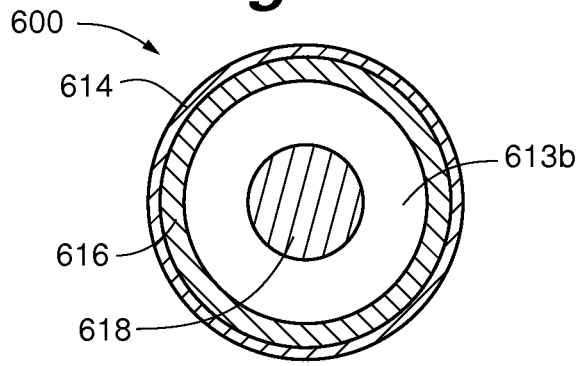
FIG. 19C is a lateral cross sectional view of the infusion section of the catheter of FIG. 14 taken through the lines 19C-19C.

FIG. 19A is a proximal lateral cross sectional view taken through infusion section 610 and illustrates the hollow fiber membrane 614, the lumen 613b, the internal support 616 and removable stylet 618. FIG. 19B is an intermediate lateral cross sectional view taken through infusion section 610 and illustrates the hollow fiber membrane 614, the lumen 613b, the internal support 616 and removable stylet 618. FIG. 19C is a distal lateral cross sectional view taken through infusion section 610 and illustrates the hollow fiber membrane 614, the lumen 613b, the internal support 616 and removable stylet 618. It is noted that the hollow fiber membrane 614 becomes progressively thinner in a distal direction as illustrated in FIGS. 19A-19C. FIG. 20 is a view of the entire catheter 600 showing, inter alia, the connector 624 attached to the proximal end 612a of the catheter body 612. It should also be mentioned that while not shown, the invention contemplates and therefore is within the scope of a non-symmetrically and non-uniformly tapered hollow fiber membrane 614.

Figure 21:
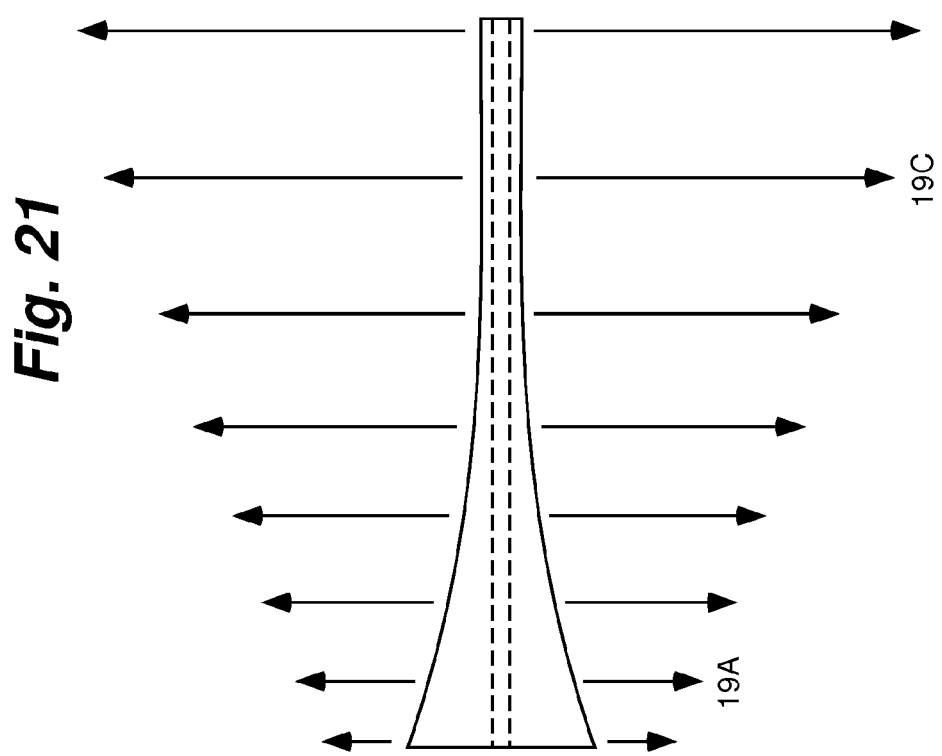
FIG. 21 illustrates the infusate distribution pattern or plume of the catheter shown in FIGS. 18-20.

FIG. 21 illustrates the infusate distribution pattern or plume of the hollow fiber section 614 catheter 600 shown in FIGS. 18-20. It is noted that the thickest section of the hollow fiber membrane 614 as illustrated in FIG. 19A, represents the closest point of infusate distribution from the hollow fiber membrane 614 while the furthest point of infusate distribution from the hollow fiber membrane 614 corresponds with the thinnest section of hollow fiber membrane 614, as illustrated in Fig. 19C. The intermediate section of hollow fiber membrane 614 represents an intermediate point of infusate distribution, as illustrated in FIG. 19B. The reason for this is that the thinner sections of the hollow fiber membrane 614 offer less resistance to the outflow of infusate and thus increases the flow at the reduced resistance regions along the length of the hollow fiber membrane 614. In some instances treatment of anatomy targeted for treatment may be more effective with a varying infusate distribution pattern.

Figure 22:
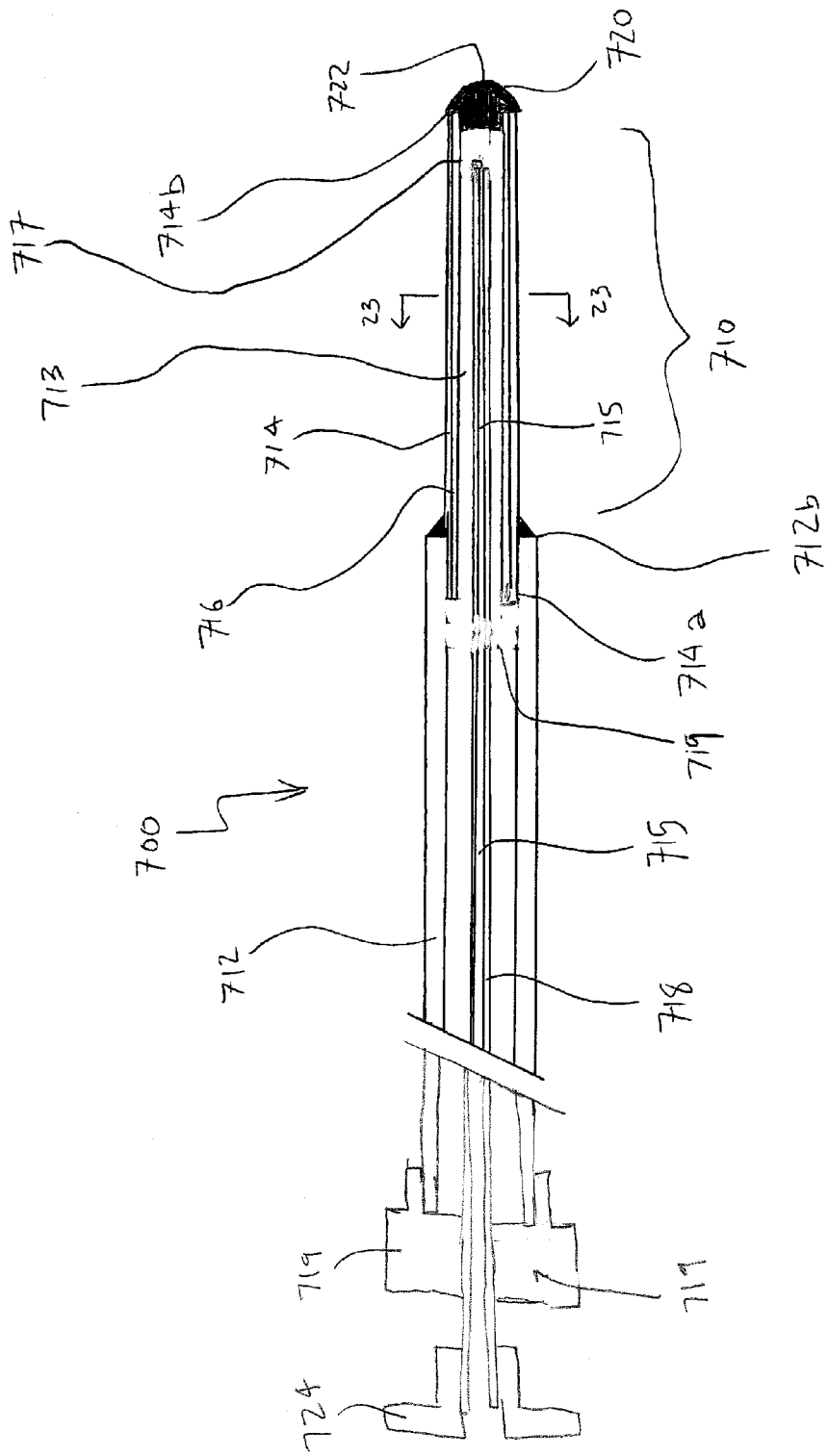
FIG. 22 is a longitudinal cross sectional view of the infusion section of an embodiment of a catheter of the present invention.

FIG. 22 shows still another embodiment of a catheter 700 of the present invention. An elongated catheter body 712 is made of any suitable flexible tubing material such as a medical grade urethane or other polymers and defines a proximal end 712a and a distal end 712b. The infusion section 710 is defined by a hollow fiber membrane 714 which is attached to the distal end 712b of the catheter body 712 using a suitable medical grade adhesive such as epoxies and urethanes and defines a proximal end 714a, and a distal end 714b. A reinforcing component is provided as an inner support tube 716 and is configured to have at least a single opening (not shown) to facilitate the delivery of infusate through the hollow fiber membrane 714, is mounted within the hollow fiber membrane 714, extends the length of the hollow fiber membrane 714, defines a first lumen 713 and serves to strengthen the infusion section 710 and catheter body 712, thus facilitating catheter 700 introduction into a patient during treatment and upon removing the stiffening stylet (not shown) prior to infusion or upon removing the catheter 700 from the patient following completion of treatment. The internal support 716 may include other types of openings other than a single hole, such as circles, slots or triangles as may be needed to create the appropriate, flexibility, strength and openness. Alternatively, the internal support can be fabricated from polymer or metallic wires to create a braided tube (not shown) having sufficient strength, openness and flexibility. The catheter 700 also has a flexible delivery tube 718 which is placed in the catheter after removing the removal stylet (not shown) defining a second lumen 715 extending through the first lumen 713 and along the length of the catheter 700 which serves to deliver infusate to the distal end 714b of the hollow fiber membrane 714. An end piece 720 is attached to the distal end 714b of the hollow fiber membrane 714 and prevents the direct escape or intrusion of fluid from the first lumen 713. A fluid seal 719 such as a Touhy Borst at the proximal end 712a of the catheter body 712 creates a sealed chamber (unnumbered) defined by the first lumen 713. A self introducing catheter 700 is advantageous for several reasons: (1) the procedure can be completed in less time; (2) the likelihood of infection is reduced due to fewer required instruments; and (3) reduced reflux of therapeutic fluid during treatment due to less tissue compression between the catheter 700 and tissue resulting from direct introduction.

Figure 23:
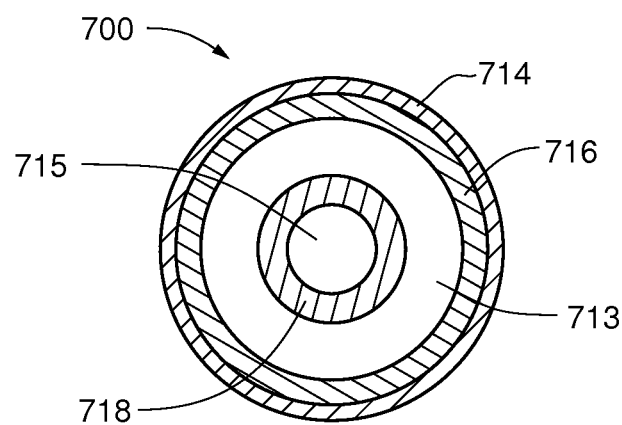
FIG. 23 is a lateral cross sectional view of the catheter of FIG. 22 taken through the lines 23-23.
Figure 24:
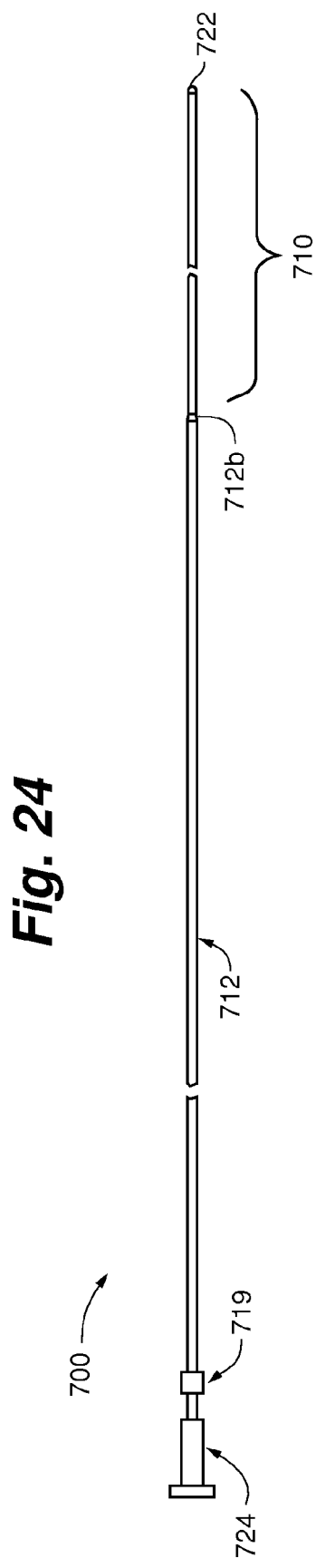
FIG. 24 is a plan view of the catheter of FIG. 22.

FIG. 23 is a lateral cross sectional view taken through infusion section 710 and illustrates the hollow fiber membrane 714, first lumen 713, internal support 716, delivery tube 718 and second lumen 715. FIG. 24 is a view of the entire catheter 700 showing, inter alia, the connector 724 attached to the proximal end (unnumbered) of the delivery tube 718.

Figure 25:
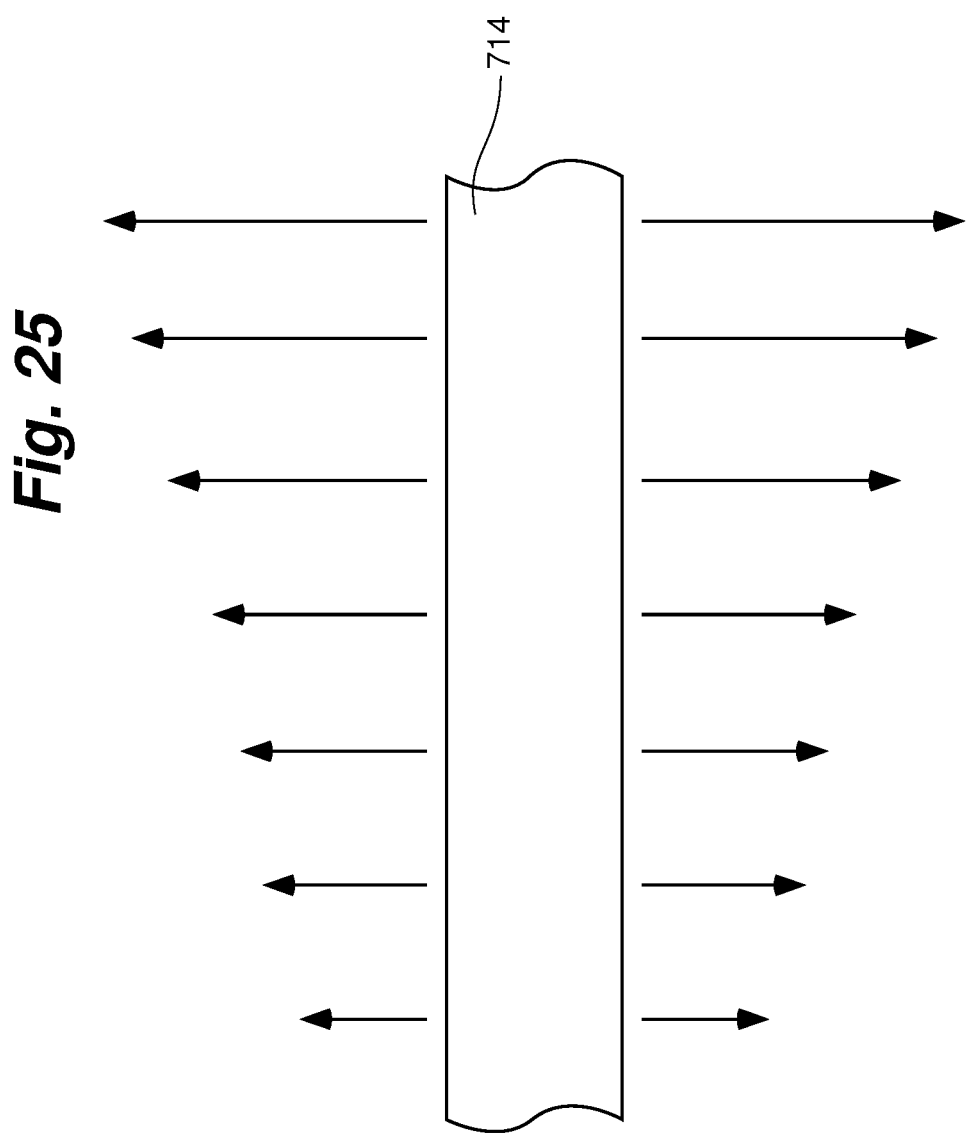
FIG. 25 illustrates the infusate diffusion pattern or plume of the catheter shown in FIGS. 22-24.

FIG. 25 illustrates the infusate distribution pattern or plume of the hollow fiber section 714 catheter 700 shown in FIGS. 22-24. It is noted that in this embodiment the hollow fiber membrane 714 has a substantially consistent diameter and thickness and that the region of furthest infusate distribution from the hollow fiber membrane 714 is most distal with the distribution becoming less from the hollow fiber membrane 714 in a proximal direction. The reason for this is that infusate is delivered by positive fluid pressure along the length of the catheter 700 via the second lumen 715 of the delivery tube 718 before emptying from the open end 717 into the first lumen 713. When the first lumen 713 is filled with infusate and after closing the fluid seal 719, the infusate will be forced first through the internal support 716 openings (not shown), then through the pore structure of the hollow fiber membrane 714 into the tissue of the patient to be treated. One of the effects of the hollow fiber membrane 714 is to substantially equalize the pressure along the length of the infusion section 710 at which the infusate is distributed to the patient. Because in this embodiment the open end 717 of the delivery tube 718 is located relatively distally, the infusate will exit the infusion section 710 at the maximum distance from the hollow fiber membrane 714. The first lumen 713 in the region of the hollow fiber membrane 714 is sufficiently small such as to create flow resistance with lumen pressure increasing from the distal region (unnumbered) to the proximal region (unnumbered) of the hollow fiber 714. This pressure drop creates the distribution pattern as represented in FIG. 25 with increased distribution at the distal region (unnumbered) of the hollow fiber membrane 714 due to the highest infusate pressure there.

Figure 26:
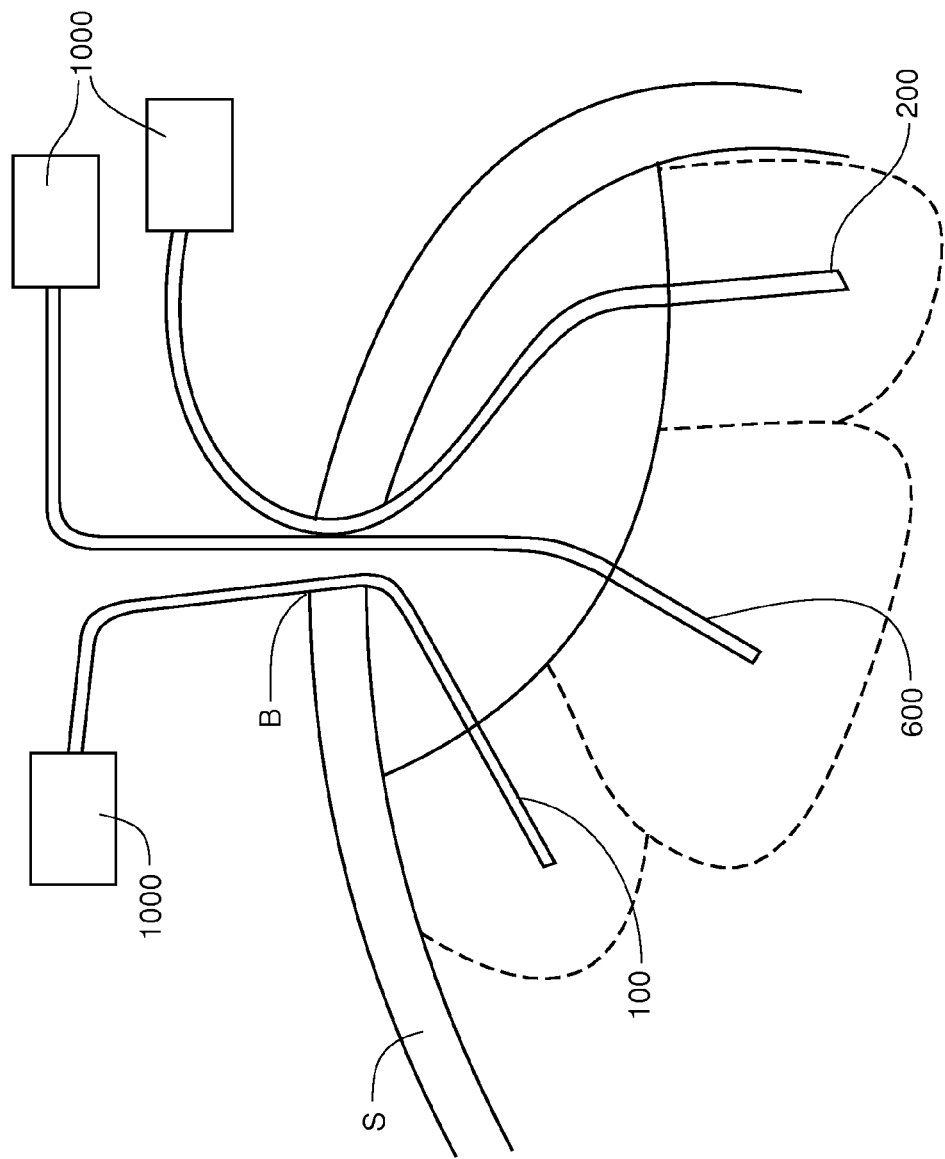
FIG. 26 is a view of the catheters of FIGS. 14 and 18 attached to an infusion pump via a distribution manifold, in place during treatment through a human skull in to a cranial cavity following surgical resectioning of a tumor, showing the relative diffusion pattern of each catheter.

FIG. 26 illustrates the deployment of the catheters 100, 200, 600 in an array to effectively cover the region closest to the brain cavity created by surgical resection of a brain tumor. It is seen that the catheters 100, 200, 600 are connected and in fluid communication with separate infusion pumps 1000. Alternatively, catheters 300, 400 could replace catheters 100, 200 to provide a similar infusate distribution plume.

Figure 27A:
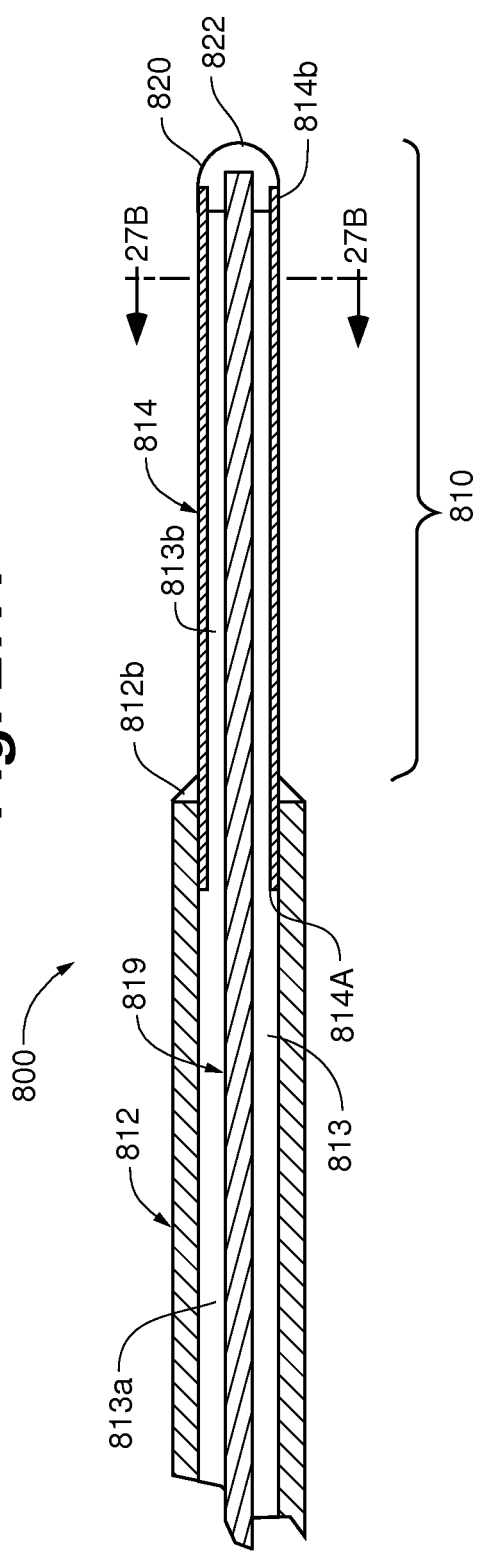
FIG. 27A is a longitudinal cross sectional view of the infusion section of an embodiment of a catheter of the present invention.

FIG. 27A is a longitudinal cross sectional view of the infusion section 810 of an embodiment of a catheter 800 of the present invention. An elongated catheter body 812 is made of any suitable flexible tubing material such as a medical grade urethane or other polymers or metals and defines a proximal end 812a, a distal end 812b and a lumen 813a capable of fluid communication, extending the length of the catheter body 812. The infusion section 810 is defined by a hollow fiber membrane 814 which is attached to the distal end 812*b* of the catheter body 812 using a suitable medical grade adhesive such as epoxies or urethanes and defines a proximal end 814*a*, a distal end 814*b* and a lumen 813*b*. The lumen 813*b* of the hollow fiber membrane 814 is continuous with the lumen 813*a* of the catheter body 812 to form lumen 813 and allows fluid communication between the proximal end 812*a* of the catheter body 812 and the distal end 814*b* of the hollow fiber membrane 814. An end piece 820 is attached to the distal end 814*b* of the hollow fiber membrane 814 and prevents the direct escape or intrusion of fluid from the lumen 813*b*.

The catheter 800 is designed to accommodate a fixed reinforcing stylet 819 through the lumen 813 which serves to stiffen the hollow fiber membrane 814 and catheter body 812, thus facilitating introduction into a patient during treatment. The stylet 819 can comprise any suitable material to provide stiffness to the hollow fiber membrane 814. For example, in certain embodiments the stylet 819 may comprise nickel titanium or nitinol. The end piece 820 therefore also provides a stop. In certain embodiments the stylet 819 provides a steering advantage for the catheter 800. For example, the stylet 819 can be subjected to torque by the user, upon application of rotational force upon a fitting 824 (see FIG. 27D) at the proximal end of the stylet 819. To improve steerability, the stylet 819 may be tapered to provide different stiffnesses along the catheter length and/or the stylet tip can be shaped in a variety of curved configurations. Accordingly, the stylet 819 and catheter 800 can be guided through a tissue mass or fluid filled organ. A self introducing catheter 800 is advantageous for several reasons: (1) the procedure can be completed in less time; (2) the likelihood of infection is reduced due to fewer required instruments; and (3) reduced backflow of therapeutic fluid during treatment due to less tissue compression between the catheter 800 and tissue resulting from direct introduction.

Figure 27B:
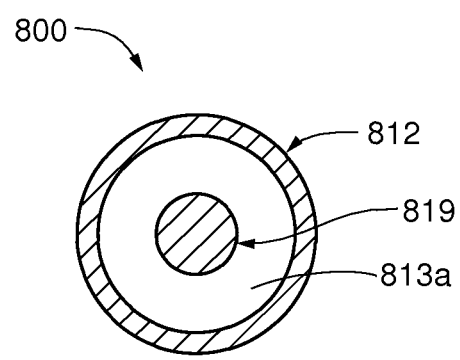
FIG. 27B is a lateral cross sectional view taken through lines 27B-27B of FIG. 17A.
Figure 27C:
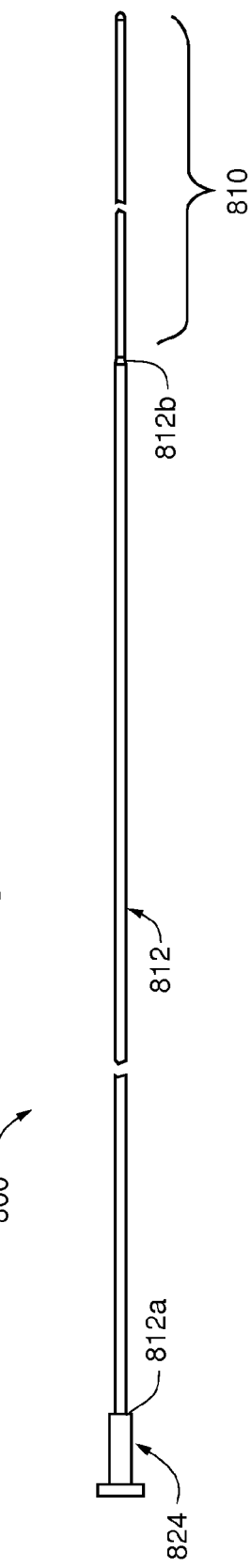
FIG. 27C is a view of the entire catheter of FIG. 27A.
Figure 27D:
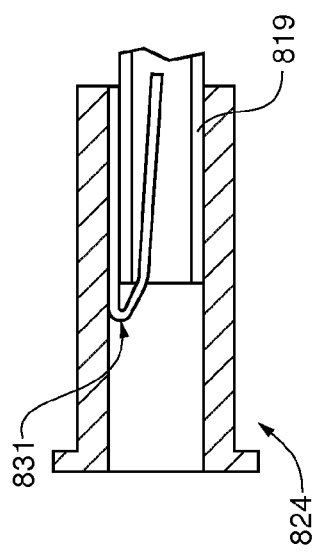
FIG. 27D is a cross sectional view of a connector coupled to a removable stylet according to an embodiment of the present invention.

FIG. 27B is a lateral cross sectional view taken through lines 27B-27B of FIG. 17A and illustrates the catheter body 812 defining the lumen 813*a*. The stylet 819 is seen extending through the lumen 813*a*. FIG. 27C is a view of the entire catheter 800, showing, inter alia, a fitting 824 attached to the proximal end 812*a* of the catheter body 812. FIG. 27D is a cross sectional view of the fitting 824 coupled to the stylet 819 with a fastener 831. The stylet 819 can also be fastened to the center of the fitting 824 concentrically with the lumen 813*a* to provide improved rotational control. A user can apply a rotational force to the fitting 824 to supply a torsional force to the stylet 819 via the fastener 831.

Figure 28A:
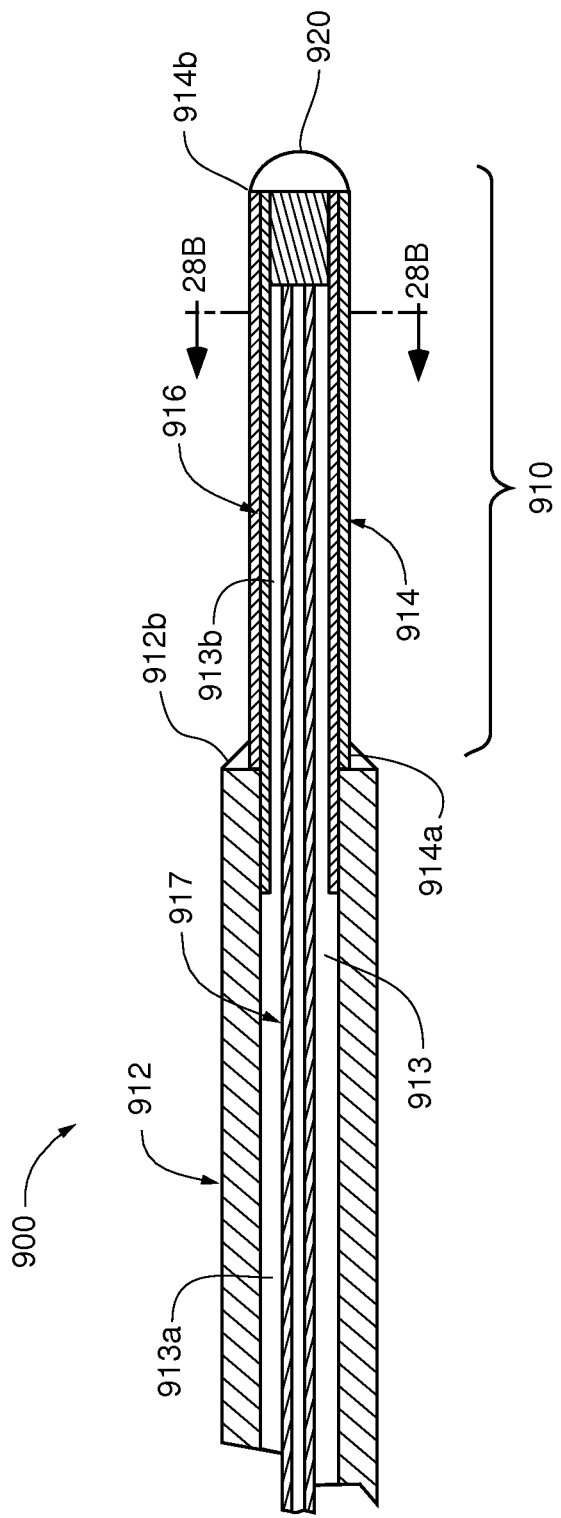
FIG. 28A is a longitudinal cross sectional view of the infusion section of an embodiment of a catheter of the present invention.

FIG. 28A is a longitudinal cross sectional view of the infusion section 910 of an embodiment of a catheter 900 of the present invention. An elongated catheter body 912 is made of any suitable flexible tubing material such as a medical grade urethane or other polymers and defines a proximal end 912*a*, a distal end 912*b* and a lumen 913*a* capable of fluid communication, extending the length of the catheter body 912. The infusion section 910 is defined by a hollow fiber membrane 914 which is attached to the distal end 912*b* of the catheter body 912 using a suitable medical grade adhesive such as epoxies or urethanes and defines a proximal end 914*a*, a distal end 914*b* and a lumen 913*b*. The lumen 913*b* of the hollow fiber membrane 914 is continuous with the lumen 913*a* of the catheter body 912 to form lumen 913 and allows fluid communication between the proximal end 912*a* of the catheter body 912 and the distal end 914*b* of the hollow fiber membrane 914. A reinforcing component is provided in the form of relatively flexible, slotted, internal support 916 made of polymers or metal within the hollow fiber membrane 914 that serves to protect and strengthen the catheter 900, thus facilitating catheter 900 introduction into a patient and facilitating the removal of a removable priming tube 917 prior to infusion and facilitating the safe removal of the catheter 900 from the patient following completion of treatment. The internal support 916 may include other types of openings other than slots, such as circles or triangles as may be needed to create the appropriate, flexibility, strength and openness. Alternatively, the internal support 916 can be fabricated from polymer or metallic wires to create a braided tube (not shown) having sufficient strength, openness and flexibility.

An end piece 920 is attached to the distal end 914*b* of the hollow fiber membrane 914 and prevents the direct escape from or intrusion of fluid into the lumen 913*b*. The catheter 900 is designed to accommodate a removable priming tube 917 through the lumen 913 which serves to prime the catheter 900 prior to infusion, and also stiffen the hollow fiber membrane 914 and catheter body 912, thus facilitating introduction into a patient during treatment. An optional, removable stylet may be inserted within the priming tube 917 to provide extra stiffness during introduction of the catheter 900. The optional stylet can then be removed prior to priming with the priming tube 917. The priming tube 917 also facilitates catheter 900 introduction into a patient, the removal of the priming tube 917 prior to infusion, and the safe removal of the catheter 900 from the patient following completion of treatment. The end piece 920 therefore also provides a stop for the priming tube 917 allowing it to sufficiently stiffen the infusion section 910 to be self-introducing into brain or other tissues. A self introducing catheter 900 is advantageous for several reasons: (1) the procedure can be completed in less time; (2) the likelihood of infection is reduced due to fewer required instruments; and (3) reduced backflow of therapeutic fluid during treatment due to less tissue compression between the catheter 900 and tissue resulting from direct introduction.

Figure 28B:
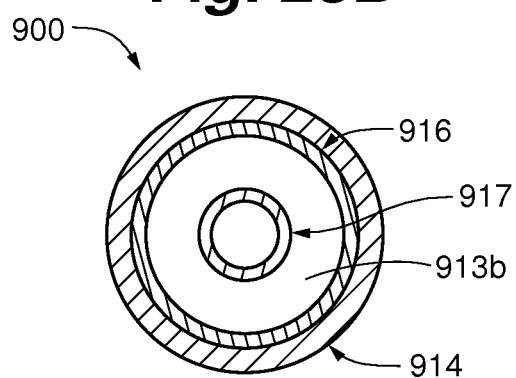
FIG. 28B is a lateral cross sectional view taken through lines 28B-28B of FIG. 28A.
Figure 28C:
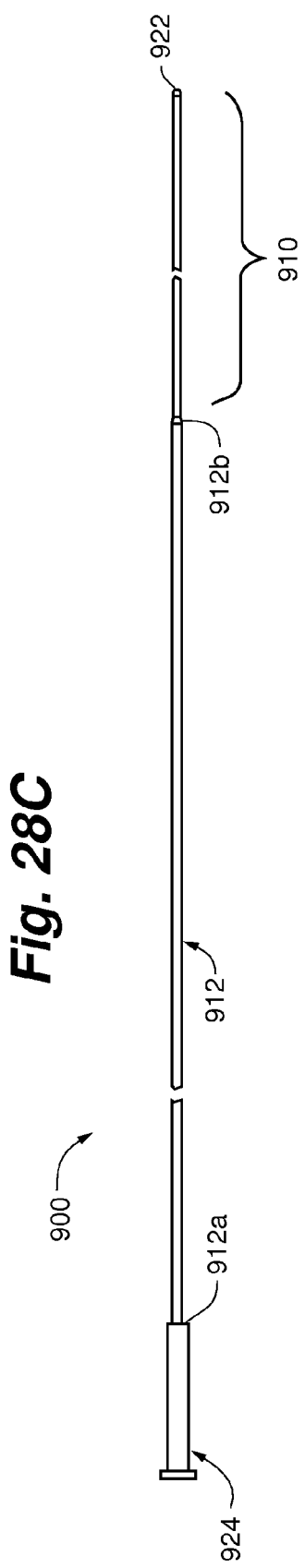
FIG. 28C is a view of the entire catheter of FIG. 28A.

FIG. 28B is a lateral cross sectional view taken through lines 28B-28B of FIG. 28A and illustrates the catheter body 912 defining the lumen 913*b*. The priming tube 917 is seen extending through the lumen 913*b*. The internal support 916 is seen defining the lumen 913*b* along with the hollow fiber membrane 914. FIG. 28C is a view of the entire catheter 900, showing, inter alia, the connector 924, with an infusate visualization feature, attached to the proximal end 912*a* of the catheter body 912. Although not shown in FIG. 28C, the priming tube 917 can be inserted within lumen 913, and can include a fitting or connector at its proximal end for infusion connection.

FIG. 29A is a longitudinal cross sectional view of the infusion section 1110 of an embodiment of a catheter 1100 of the present invention. An elongated catheter body 1112 is made of any suitable flexible tubing material such as a medical grade urethane or other polymers or metals and defines a proximal end 1112*a*, a distal end 1112*b* and a lumen 1113*a* capable of fluid communication, extending the length of the catheter body 1112. The infusion section 1110 is defined by a hollow fiber membrane 1114 which is attached to the distal end 1112*b* of the catheter body 1112 using a suitable medical grade adhesive such as epoxies or urethanes and defines a proximal end 1114*a*, a distal end 1114*b* and a lumen 1113*b*. The lumen 1113*b* of the hollow fiber membrane 1114 is continuous with the lumen 1113*a* of the catheter body 1112 to form lumen 1113 and allows fluid communication between the proximal end 1112*a* of the catheter body 1112 and the distal end 1114*b* of the hollow fiber membrane 1114. The catheter 1100 is designed to accommodate a includes a stylet 1115 through the lumen 1113 which serves to stiffen the hollow fiber membrane 1114 and catheter body 1112. The stylet 1115 also facilitates catheter 1100 introduction into a patient and the safe removal of the catheter 1100 from the patient following completion of treatment.

The stylet 1115 includes a tip 1123 attached to the distal end 1115b of the stylet 1115. The tip 1123 may be formed integrally with the stylet 1115, or formed separately and then attached. The tip 1123 and distal end 1115b of the stylet 1115 are fastened to the distal end 1114b of the hollow fiber membrane 1114 with an adhesive 1125. The stylet 1115 can thus sufficiently stiffen the infusion section 1110 to be self-introducing into brain or other tissues. In addition, the tip 1123 prevents the direct escape from or intrusion of fluid into the lumen 1113b. The tip 1123 can take a number of forms. In one embodiment the tip 1123 is formed in a ball or spherical shape. Accordingly, the round front side of the tip 1123 can facilitate the self introduction of the catheter 1100. A self introducing catheter 1100 is advantageous for several reasons: (1) the procedure can be completed in less time; (2) the likelihood of infection is reduced due to fewer required instruments; and (3) reduced backflow of therapeutic fluid during treatment due to less tissue compression between the catheter 1100 and tissue resulting from direct introduction.

Figure 29B:
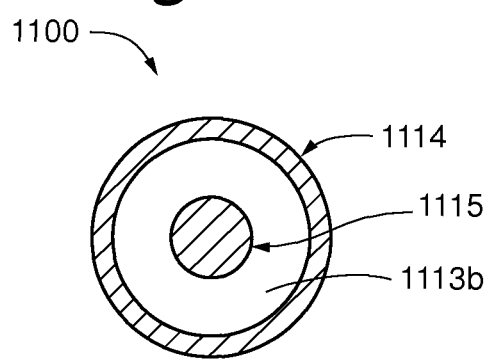
FIG. 29B is a lateral cross sectional view taken through lines 29B-29B of FIG. 29A.

FIG. 29B is a lateral cross sectional view taken through lines 29B-29B of FIG. 29A and illustrates the hollow fiber membrane 1114 defining the lumen 1113b.

Figure 30A:
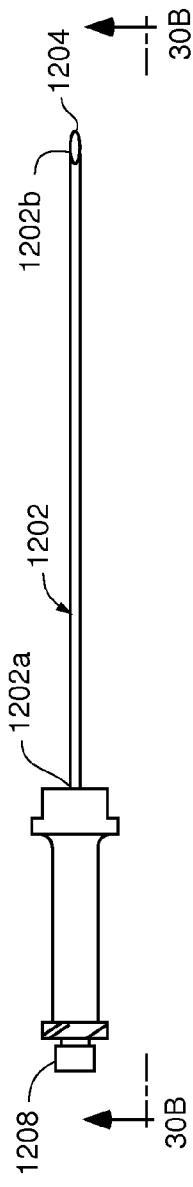
FIG. 30A is a plan view of an introducer used to introduce various embodiments of a catheter according to an embodiment of the present invention.

FIG. 30A is a plan view of an introducer 1200 used to introduce various embodiments of the catheter 100, 200, 300, 400, 500, 600, 700, 800, 900, 1100 into a brain or other tissues according to certain embodiments of the invention. While in certain embodiments a catheter of the invention may be self-introduced without the introducer 1200, in certain embodiments the introducer 1200 can also be used to ease insertion. The introducer 1200 includes a needle 1202 extending between a proximal end 1202a and a distal end 1202b. The needle 1202 can comprise stainless steel and includes an open tip 1204 at the distal end 1202b providing access to an inner lumen of the needle. At the proximal end 1202a, the needle is coupled with a hub 1206. The hub 1206 includes a vent plug 1208 at its proximal end, which is adapted to receive one of the various embodiments of the catheter of the invention. The introducer 1200 can be used alone or in conjunction with a sheath, as shown in FIG. 30C.

Figure 30B:
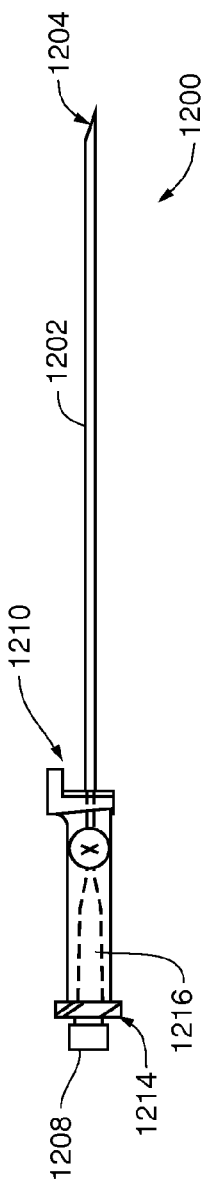
FIG. 30B is a longitudinal cross sectional view of FIG. 30A, taken along line 30B-30B.

FIG. 30B is a longitudinal cross sectional view of FIG. 30A, taken along line 30B-30B. The hub 1206 includes a locking portion 1210 that can secure the hub 1206 to a sheath hub 1212 as shown in FIG. 30C. The hub 1206 includes a connector lock portion 1214 to secure the catheter connector to the hub 1206 in some embodiments. As shown in FIG. 30B, the hub 1206 also includes a relief portion 1216, which can guide insertion of the catheter into the needle lumen.

Figure 30C:
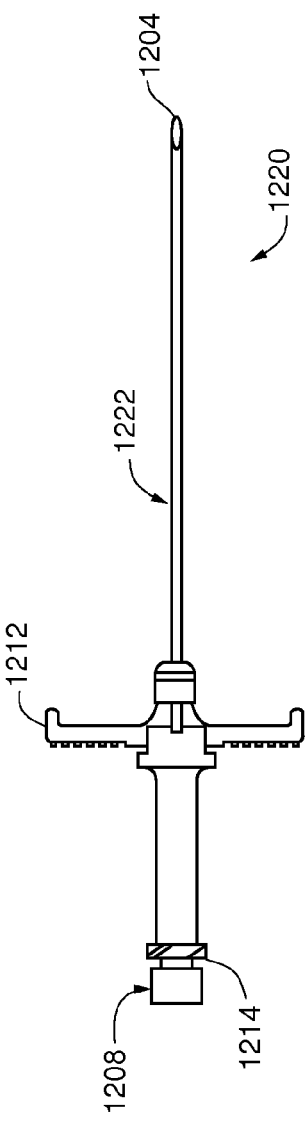
FIG. 30C is a plan view of an introducer assembly including an introducer and a sheath according to an embodiment of the present invention.

FIG. 30C is a plan view of an introducer assembly 1220 including the introducer 1200 coupled to the sheath hub 1212, with a sheath 1222 coupled to the sheath hub about the needle 1202 of introducer. The sheath hub 1212 can secure the sheath 1222 in place as the catheter is introduced into the adjacent tissue.

In certain embodiments, the sheath 1222 comprises a "tear-away" plastic sheath placed over the needle 1202. Accordingly, in some cases the introducer 1200 comprises a sterile disposable introducer that provides an access to a targeted muscle or other tissue compartment to facilitate the placement of catheters according to embodiments of the invention. According to some embodiments, in a first step, the sharp-tipped needle 1202 and sheath 1222 are inserted through the skin and into the targeted tissue compartment. Once properly positioned, the needle 1202 is removed leaving the hollow tear-away sheath 1222 in place. One of the various catheters provided in embodiments of the invention can then be placed through the hollow sheath 1222 and into the tissue compartment. Once the catheter is placed, the sheath 1222 is designed to easily tear away for removal. In some cases the needle 1202 and sheath 1222 are similar in respects to those used for cardiovascular or percutaneous access devices. For example, the sheath 1222 can comprise a thin walled polyethylene tubing. The introducer 1200 can comprise a stainless steel needle 1202 with a three-facet sharp tip point 1204.

Use

Using the various embodiments of the catheter of the present invention following the creation of a burr hole B in the patient's skull S involves initially introducing the catheter into tissue through the burr hole B to the treatment site, then removing the stylet. This is followed by inserting a priming tube such as delivery tube 718 having a similar outer dimension as the removable stylet into the lumen and priming the catheter under pressure with infusate. This procedure is necessary to remove air and other gases from the catheter prior to initiating treatment. In some embodiments, a priming tube such as tube 917 can serve to introduce the catheter without a separate stylet, and then be used to prime the catheter. In the case of the catheter 300, the infusion port 318 is filled with infusate prior to introducing the catheter 300 and capped. The priming tube is next removed while infusing the priming tube for some catheters to insure no additional air is introduced into the catheter during priming tube removal. Using the connector the catheter is attached to an infusion pump 1000 which provides a controlled amount of positive fluid pressure, causing the infusate to be distributed through the hollow fiber. Following completion of the procedure, the catheter is disconnected from the infusion pump 1000, removed from the treatment site and disposed of.

EXAMPLE 1

Infusion Procedure for Pig Brain MRI Contrast Study

Materials and Methods

Pretest Setup with Pressure Monitoring 1.1 Fill a 10 ml syringe 2000 (FIG. 31) with the desired infusate mixture. Connect a three-way valve 2002 to the 10 ml syringe with the T of the three-way valve pointing up. Connect a two-way valve 2004 off of the straight section of the three-way valve.

Figure 31:
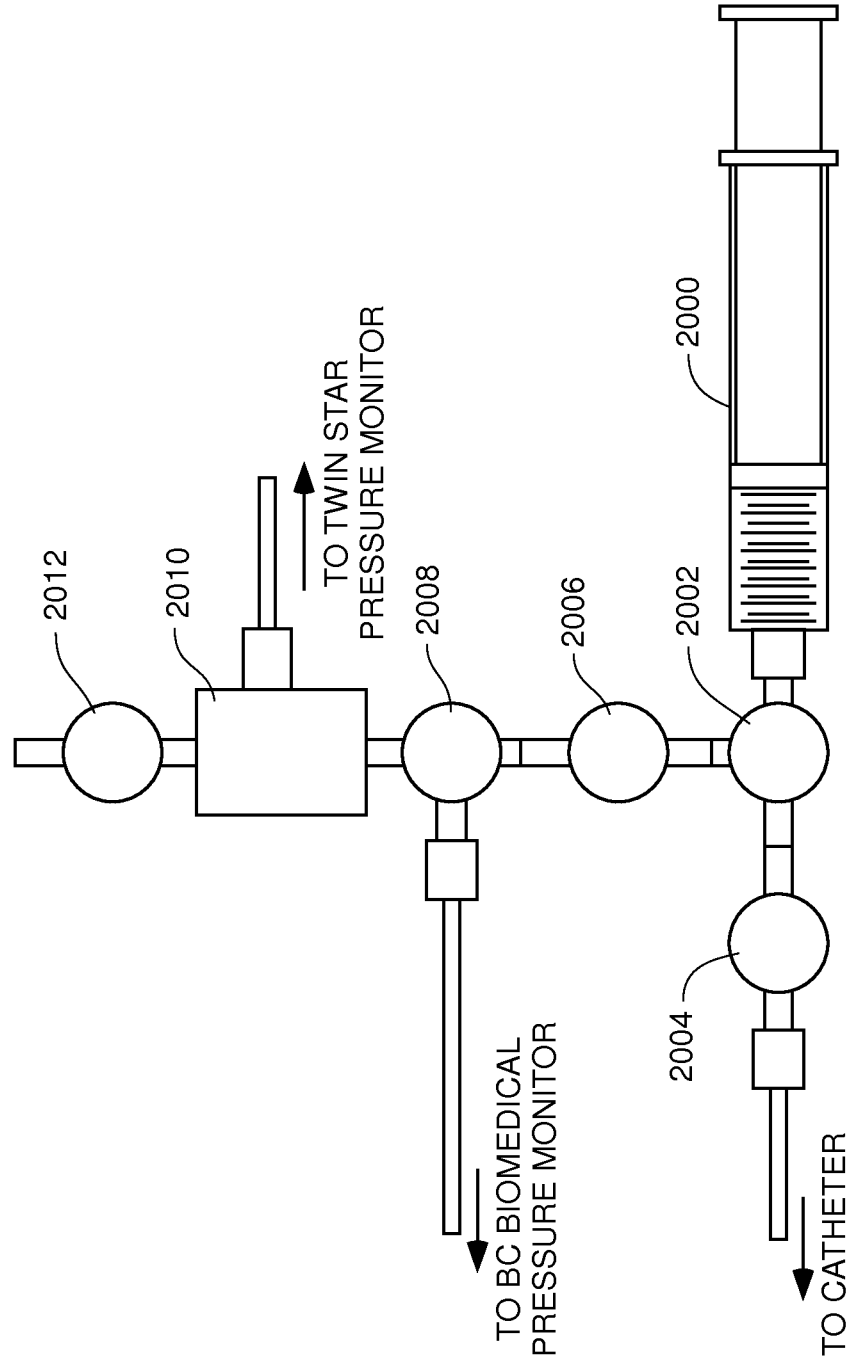
FIG. 31 is a diagram of a valve assembly according to an embodiment of the present invention.

1.2 Going up from the three way valve 2002 attach a two-way valve 2006, then another three-way valve 2008, valve 4, then an Edwards Lifesciences PX600 pressure transducer 2010 with valve 2012 on the transducer positioned on the top (FIG. 31).

1.3 Connect a Medex 536040 line to valve 2008, leave the other end open, it will later be attached to the BC Biomedical pressure monitor. Attach the cord from the pressure transducer 2010 to the Twin Star pressure monitor (FIG. 31).

1.4 Connect a Medex 536040 line to valve 2004 (FIG. 31). Leave the end of the tubing that is to connect to the catheter open for now.

Figure 32:
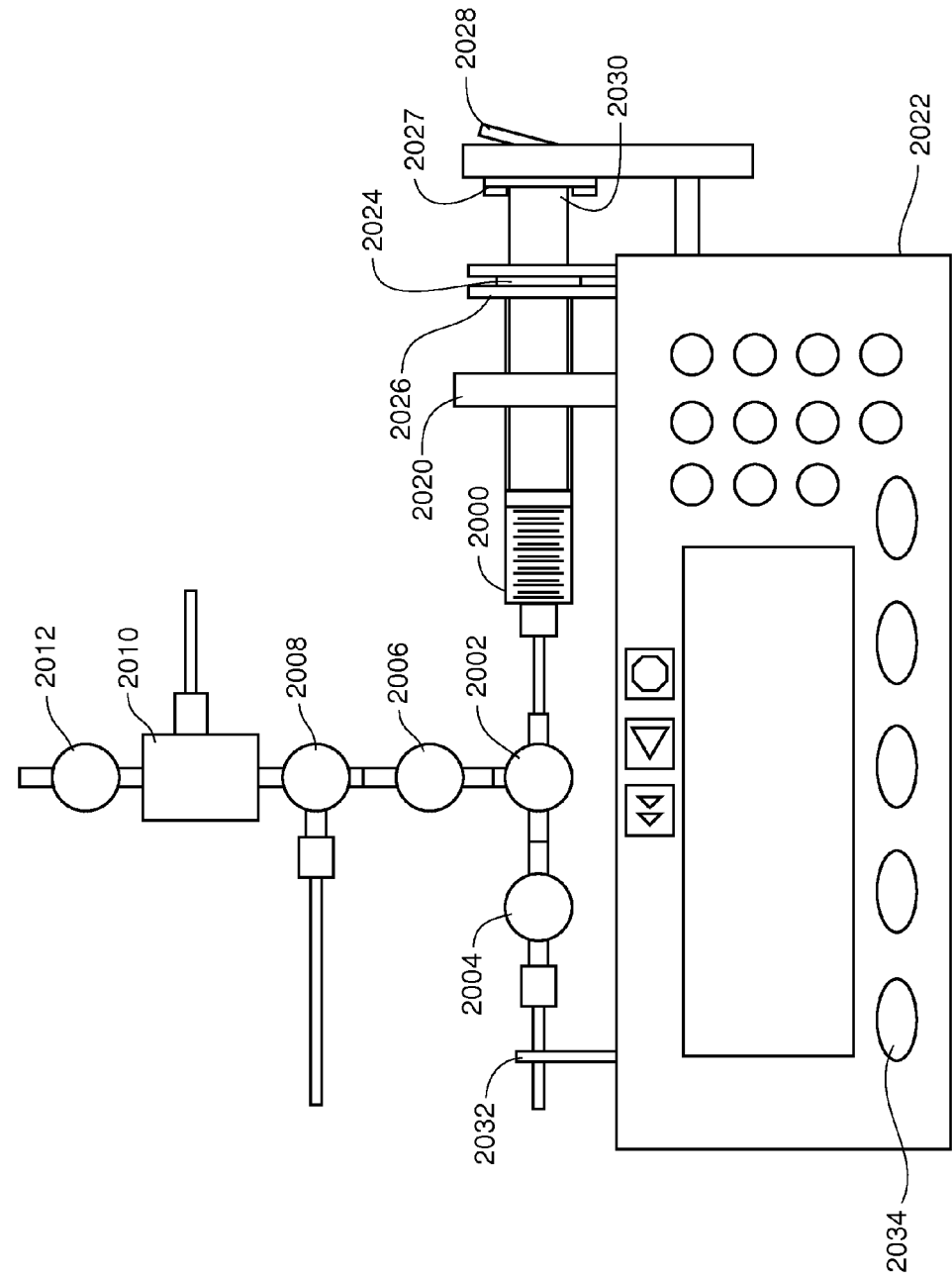
FIG. 32 is an illustration of the valve assembly of FIG. 31 coupled with a syringe plunger apparatus according to an embodiment of the present invention.

1.5 Lift the syringe barrel clamp 2020 and slide the syringe 2000 and valve assembly into the slot on the top of the pump 2022 (FIG. 32).

1.6 Place the flange 2024 of the syringe 2000 into the syringe barrel flange clip 2026 to secure the syringe (FIG. 32).

1.7 Open the syringe plunger holders 2027 by squeezing the syringe plunger 2030 release lever 2028, slide the plunger holders over until they are flush with the plunger 2030 of the syringe and then release the syringe plunger holders to secure the plunger 2030 in place (FIG. 32).

1.7.1 Run the tubing through the tubing holders 2032 to secure the tubing to the pump (FIG. 32).

1.8 Record the date, start time, fiber length, infusion rate, lot number, and catheter number in the test setup of each catheter being tested.

1.9 Prime all of the lines, fittings, and valves using the bolus button 2034 on the pump 2022. Press and hold the bolus button 2034 with all of the valves open. When infusate comes out of valve 2012 close valve 2012. When it comes out of the end of the tubing attached to valve 2008 attach the line to the BC Biomedical pressure monitor, be sure that the BC Biomedical pressure monitor is filled with fluid before connecting. Continue to hold the bolus button 2034 until infusate is coming out of the line attached to valve 2004 (FIG. 31).

1.10 While holding the end of the line coming from tubing holders even with the pressure transducer zero the pressure monitors. After zeroing the monitors close valve 2012.

Pretest Setup without Pressure Monitoring 2.1 Fill a 10 ml syringe with the desired infusate mixture.

2.2 Connect a Medex 536040 line to the syringe. Leave the end of the tubing that is to connect to the catheter open for now.

2.3 Lift the syringe barrel clamp and slide the syringe into the slot on the top of the pump (FIG. 32).

2.4 Place the flange of the syringe into the syringe barrel flange clip to secure the syringe (FIG. 32).

2.5 Open the syringe plunger holders by squeezing the syringe plunger release lever, slide the plunger holders over until they are flush with the plunger of the syringe and then release the syringe plunger holders to secure the plunger in place (FIG. 32).

2.6 Run the tubing through the tubing holders to secure the tubing to the pump (FIG. 32).

2.7 Record the date, start time, fiber length, infusion rate, lot number, and catheter number in the test setup of each catheter being tested.

2.8 Prime the line by pressing and holding the bolus button. Continue to hold the bolus button until infusate is coming out of the luer fitting.

4 Step Catheter Placement

Step 1: Catheter Insertion 3.1 Insert the priming tube completely into the catheter.

3.2 If using the optional support stylet for superior positioning, insert the support stylet into the priming tube completely and connect the luer fittings.

3.3 Insert the catheter into the brain and guide the hollow fiber on the distal end of the catheter to the desired region of the brain.

3.4 Secure the catheter so that it is not moved during the priming, tunneling, or infusion process.

3.5 Remove the support stylet from the priming tube (if used in step 3.2). It is important to follow catheter priming procedure to prevent air bubbles in the catheter. In addition, it is important to maintain prime and no air bubbles in catheter and infusion lines during catheter insertion, tunneling and fitting attachment.

Step 2: Priming the Catheter 4.1 Attach a syringe filled with infusate to the male/female luer fitting attached to the priming tube.

4.2 Unlock the priming tube luer fitting from the female/female connector luer fitting attached to the catheter body.

4.3 Inject infusate at a steady rate into the catheter through the priming tube until the level of the infusate reaches luer fitting at the proximal end of the catheter body.

4.4 Continue to rapidly inject infusate while pulling the priming tube out of the catheter body. The female/female luer fitting should be full when the priming tube is removed.

Step 3: Tunneling the Catheter 5.1 Cut off the proximal luer fitting from the catheter body with a scissors and discard the luer fitting.

5.2 Attach the small tipped trocar to the proximal end of the catheter body.

5.3 Tunnel the catheter subcutaneously for several cm from the entry point.

5.4 After tunneling the catheter cut off the trocar from the catheter body with a scissors.

Figure 33:
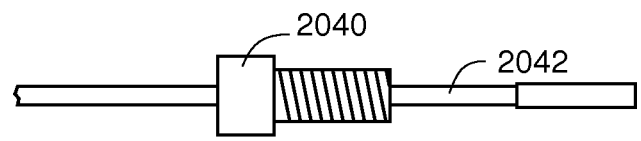
FIGS. 33-35 are perspective views showing the attachment of a distal compression fitting according to an embodiment of the present invention.

Step 4: Attaching the Distal Compression Fitting 6.1 Slide the flangeless nut 2040 over the catheter body 2042, with the nut threads facing proximally (FIG. 33).

Figure 34:
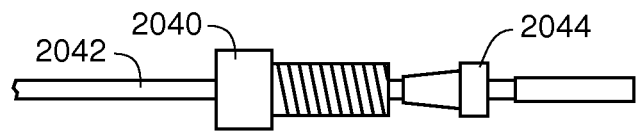

6.2 Slip the ferrule 2044 over the catheter body, with the tapered portion of the ferrule facing toward the nut (FIG. 34).

Figure 35:
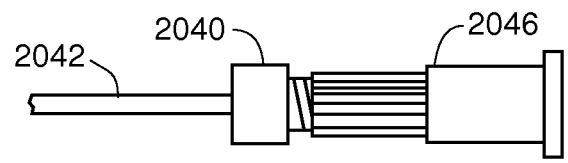

6.3 Insert the tubing with the ferrule in place into the receiving port 2046, and, while holding the tubing down firmly into the port, tighten the receiving port onto the nut finger tight (FIG. 35).

6.4 Remove the nut and confirm that the proximal end of the catheter is flush with the top of the ferrule. Any excess of the catheter tubing could lead to leaking from the fitting. Cut off any excess flush with the ferrule.

6.5 Retighten the red receiving port onto the nut.

6.6 Fill the nut with luer attachment with infusate; be sure that there are no air bubbles in the system.

6.7 Attach the line from the tubing holders to the luer fitting on the red nut. Both fittings should be completely filled with infusate so no air is entrapped in the catheter.

Running the Infusion with Pressure Monitoring 7.1 Set the flow rate on the infusion pump.

7.2 Start the infusion pump, then the pressure monitors and a timer immediately after.

7.3 Observe the pressures being recorded. If the catheter is not building any pressure check and tighten fittings that may be leaking 7.4. If pump and monitors are to be removed for MRI images, press stop on the pump, options, choose option one—standby and after entering an adequate amount of time press enter and then complete step 7.4.1 to 7.4.5.

7.4.1 Close valves 2004 and 2006 (FIG. 31).

7.4.2 Disconnect valve 2008 from valve 2006. Remove the tubing from the tubing holders 2002 (FIG. 32).

7.4.3 Release the syringe plunger holders and slide the syringe plunger release lever out of the way.

7.4.4 Pull up on the syringe barrel clamp and carefully remove the syringe flange from the syringe barrel flange clip (FIG. 32). Place the syringe and tubing in the coil with the gel container and take images as needed.

7.4.5 To reattach the syringe and continue to infuse follow steps 1.5 to 1.8, then reattach valve 2006 to valve 2008, be sure that no air is allowed into the system. Open valves 2004 and 2006 and press start on the pump (FIG. 31).

Running the Infusion without Pressure Monitoring 8.1 Set the flow rate on the infusion pump.

8.2 Start the infusion pump, then a timer immediately after.

8.3. If pump is to be removed for MRI images, press stop on the pump, options, choose option one—standby and after entering an adequate amount of time press enter then follow steps 8.3.1 to 8.3.4.

8.3.1 Remove the tubing from the tubing holders (FIG. 31).

8.3.2 Release the syringe plunger holders and slide the syringe plunger release lever out of the way.

8.3.3 Pull up on the syringe barrel clamp and carefully remove the syringe flange from the syringe barrel flange clip (FIG. 32). Place the syringe and tubing in the coil with the gel container and take images as needed.

8.3.4 To reattach the syringe and continue to infuse follow steps 1.5 to 1.8 and press start on the pump (FIG. 31).

Experimental Protocol

A tumor infusion animal (porcine) study was performed using a system as described herein. Burr holes were created on both the left and right sides of the skull, burr holes were 1 cm deep. A Vygon™ catheter was placed on the left side and inserted 3 cm from the skull surface. The Vygon™ catheter was primed with a syringe as it would be in a standard surgical procedure. The Vygon catheter was then tunneled through the scalp. A polycarbonate plate was secured to the skull with two titanium screws over the right burr. The catheter (1 cm hollow fiber length) was inserted through the o-ring in the plate a depth of 3 cm. In some embodiments, the polycarbonate plate and o-ring could alternatively comprise a bioabsorable material. The catheter was primed using a Springusor™ pump to control the rate of flow during priming. The o-ring maintained the position of the catheter while it was tunneled. Both catheters were secured with stitches and the scalp sutured shut.

After catheters were placed, the animal was wheeled over to MRI. A baseline MRI was taken, the pig remained in a prone position during the entire imaging and infusion process. Placement of both catheters looked good. There was no backflow visible for the catheter and air bubbles and backflow were visible for the Vygon catheter.

The infusion was started following the baseline MRI. Both pumps were set at 3 uL/min, pressure was monitored on a catheter of this invention with a BC Biomedical™ pressure monitor. The pressure limit on the pumps was switched to the high setting. After 2 hours (360 uL), infusion was stopped and a second MRI taken. A vitamin E capsule was placed on the right side for identification purposes. For the MRI, infusion lines were disconnected at the catheter connectors (stopcocks were closed, and lines disconnected and capped).

Catheters were re-connected and infusion re-started until the pressure level on the Medfusion pump supplying the catheter hit it upper limit at 0.7350 ml infused (slightly over 3 hours of infusion time). The lines again were disconnected and a third MRI was taken. The infusate was 0.1% Magnevist™ solution. The contrast agent showed up well on the MR images.

The compression fitting used with the catheter in the last procedure (shown in FIGS. 33-35) was replaced with a modified Vygon™ compression fitting with a smaller diameter stainless tube to fit the ID of the catheter. This worked well and was noted to be an improvement over the previous design illustrated in FIGS. 33-35.

The plate securing the catheter in place had to be modified to fit into the area on the scalp where it was to be secured to the skull. After cutting it down to size and screwing it in place it was effective in holding the catheter steady. Removing the catheter after the procedure was finished was not difficult and the catheter remained intact after removing it through the plate and out the tunneling pathway. Priming the hollow fiber catheter with the Springfusor™ pump provided improved properties as compared to manual syringe priming using a priming tube. While it took a few seconds longer to prime, it was a more simple process and the controlled flow rate provided by the pump was helpful.

Distribution with the catheter was good and there was no backflow into the burr hole. The Vygon™ catheter had a large volume of air infused and had backflow present and limited contrast agent distribution.

In conclusion, it can be seen that a catheter of the present invention was able to improve infusate distribution to the brain tissue target within close proximity of the hollow fiber membrane member without backflow.

What is claimed is:

1. A catheter, comprising:
    a. a flexible catheter body defining a length, a proximal end and a distal end;
    b. a reinforced hollow fiber porous membrane defining a length, a proximal end and a distal end, the hollow fiber membrane attached to the catheter body and defining a common lumen along the combined length of the catheter body and the hollow fiber membrane, the lumen capable of fluid communication;
    wherein the catheter comprises a catheter body, hollow fiber region, and one or more reinforcing component(s), which together provide a catheter having sufficient structural integrity for the hollow fiber region to be positioned within a body tissue; and,
    wherein the hollow fiber membrane defines an infusion section capable of infusing liquids through its pores.

2. The catheter of claim 1 wherein the hollow fiber membrane is attached to the distal end of the catheter body.

3. A catheter according to claim 1 wherein the catheter body comprises a substantially solid body portion adapted to be coupled with and extend proximally from a hollow fiber region, together with one or more reinforcing components, adapted to provide the hollow fiber region with sufficient properties to permit the hollow fiber region to be positioned and to remain in place and used to deliver and/or recover fluids.

4. A catheter according to claim 1 wherein the one or more reinforcing component(s) comprise a removable rigid stylet adapted to reinforce the catheter for insertion into tissue.

5. A catheter according to claim 1 wherein the one or more reinforcing components comprise one or more relatively flexible rods or tubes.

6. A catheter according to claim 1 wherein the reinforcing component(s) are selected from the group consisting of:
    a) a safety wire attached proximate the distal end of a hollow fiber membrane and inside the distal end of the catheter body, thereby serving to further secure the hollow fiber membrane to the catheter body;
    b) a relatively flexible, slotted, external support that substantially surrounds the hollow fiber membrane and, and in turn, serves to protect and strengthen it;
    c) a relatively flexible inner lumen tube that extends substantially the length of the catheter and that defines a central lumen, and which serves to protect and strengthen it;
    d) an inner support tube configured to have at least a single opening to facilitate the delivery of infusate through the hollow fiber membrane, the tube being mounted within the hollow fiber membrane, extending substantially the length of the hollow fiber membrane and defining a lumen and serves to strengthen the catheter.

7. A catheter according to claim 1, wherein the catheter is primed with infusate.

8. A catheter according to claim 1, wherein the catheter is steerable.

9. A catheter according to claim 1 wherein the one or more reinforcing component(s) comprise both a removable rigid stylet adapted to reinforce the catheter for insertion into tissue and an inner support tube configured to have at least a single opening to facilitate the delivery of infusate through the hollow fiber membrane, the tube being mounted within the hollow fiber membrane, extending substantially the length of the hollow fiber membrane and defining a lumen and serves to strengthen the catheter.

10. A method of delivering infusate to the body, the method comprising:
   a. providing a catheter according to claim 1,
   b. positioning the catheter within the body by means of a stylet, and removing the stylet, and
   c. delivering infusate to the body through the hollow fiber membrane provided by the catheter.

11. A method according to claim 10 wherein the one or more reinforcing component(s) comprise both a removable rigid stylet adapted to reinforce the catheter for insertion into tissue and an inner support tube configured to have at least a single opening to facilitate the delivery of infusate through the hollow fiber membrane, the tube being mounted within the hollow fiber membrane, extending substantially the length of the hollow fiber membrane and defining a lumen and serves to strengthen the catheter.

12. A catheter, comprising:
   a. a flexible catheter body defining a length, a proximal end and a distal end;
   b. a reinforced hollow fiber porous membrane defining a length, a proximal end and a distal end, the hollow fiber membrane attached to the catheter body and defining a common lumen along the combined length of the catheter body and the hollow fiber membrane, the lumen capable of fluid communication;
   wherein the catheter comprises a catheter body, hollow fiber region, and one or more reinforcing component(s), which together provide a catheter having sufficient structural integrity for the hollow fiber region to be positioned within a body tissue; and,
   wherein the porous hollow fiber membrane defines a delivery/recovery section capable of delivering and/or recovering fluids through its pores.

13. A catheter according to claim 12, wherein fluid is delivered and/or recovered through substantially the length of the hollow fiber membrane.

14. A catheter according to claim 12, wherein the catheter provides a predetermined distribution pattern in the course of infusing fluids.

15. A catheter according to claim 12 wherein the reinforcing component(s) are selected from the group consisting of:
   a) a safety wire attached proximate the distal end of a hollow fiber membrane and inside the distal end of the catheter body, thereby serving to further secure the hollow fiber membrane to the catheter body;
   b) a relatively flexible, slotted, external support that substantially surrounds the hollow fiber membrane and, and in turn, serves to protect and strengthen it;
   c) a relatively flexible inner lumen tube that extends substantially the length of the catheter and that defines a central lumen, and which serves to protect and strengthen it;
   d) an inner support tube configured to have at least a single opening to facilitate the delivery of infusate through the hollow fiber membrane, the tube being mounted within the hollow fiber membrane, extending substantially the length of the hollow fiber membrane and defining a lumen and serves to strengthen the catheter, and
   wherein fluid is delivered and/or recovered through the length of the hollow fiber membrane.

16. A catheter according to claim 15 wherein the catheter provides a predetermined distribution pattern in the course of infusing fluids.

* * * * *